United States Patent
Matsuyama et al.

(10) Patent No.: US 6,686,172 B2
(45) Date of Patent: Feb. 3, 2004

(54) METHOD OF MEASURING TOTAL HOMOCYSTEINE

(75) Inventors: Naoto Matsuyama, Takatsuki (JP); Mina Fukuhara, Osaka (JP); Masaharu Takayama, Ibaraki (JP); Koji Mizuno, Kyoto (JP)

(73) Assignee: Azwell, Inc., Osaka (JP)

( * ) Notice: Subject to any disclaimer, the term of this patent is extended or adjusted under 35 U.S.C. 154(b) by 78 days.

(21) Appl. No.: 10/069,847

(22) PCT Filed: Jun. 29, 2001

(86) PCT No.: PCT/JP01/05679
§ 371 (c)(1),
(2), (4) Date: Feb. 28, 2002

(87) PCT Pub. No.: WO02/02802
PCT Pub. Date: Jan. 10, 2002

(65) Prior Publication Data
US 2002/0123088 A1 Sep. 5, 2002

(30) Foreign Application Priority Data

Jun. 30, 2000 (JP) .......................... 2000-198094
Sep. 14, 2000 (JP) .......................... 2000-280713

(51) Int. Cl.$^7$ .......................... C12Q 1/34; C12Q 1/37; G01N 33/53
(52) U.S. Cl. .......................... 435/18; 435/23; 435/24; 435/25; 435/968; 435/975
(58) Field of Search .......................... 435/18, 23, 24, 435/25, 968, 975

(56) References Cited

U.S. PATENT DOCUMENTS

| | | | |
|---|---|---|---|
| 5,885,767 A | 3/1999 | Rozzell, Jr. | 435/4 |
| 5,998,191 A | 12/1999 | Tan et al. | 435/232 |
| 6,020,206 A | 2/2000 | Vargeese et al. | 436/89 |

FOREIGN PATENT DOCUMENTS

| | | |
|---|---|---|
| JP | 55-064800 A | 5/1980 |
| JP | 57-008797 A | 1/1982 |
| JP | 9-512634 A | 12/1997 |
| JP | 10-114797 A | 5/1998 |
| JP | 2000-166597 A | 12/1998 |
| JP | 2870704 B2 | 1/1999 |
| JP | 2001-17198 A | 7/1999 |
| JP | 2001-149092 A | 11/1999 |
| JP | 2000-502262 A | 2/2000 |
| WO | WO 93/15220 A1 | 8/1993 |
| WO | WO 95/30151 A1 | 11/1995 |
| WO | WO 98/07872 A1 | 2/1998 |
| WO | WO 99/05311 A1 | 2/1999 |

OTHER PUBLICATIONS

Kajander et al, Biochemical Journal, V.193(2), p503–512, Feb. 1, 1981 (Abstract Only).*
Ueland, P. M., International Journal Of Biochemistry, V.14(3), p207–213, (1982) (Abstract Only).*

(List continued on next page.)

Primary Examiner—Louise N. Leary
(74) Attorney, Agent, or Firm—Webb Ziesenheim Logsdon Orkin & Hanson, P.C.

(57) ABSTRACT

The present invention provides a method and a kit for detecting or quantitatively determining homocysteine rapidly and simply and with high sensitivity by oxidizing the residual homocysteine cosubstrate, the produced homocysteine-converting enzyme product or an enzyme reaction product thereof in the presence of an SH reagent to produce hydrogen peroxide and determining the produced hydrogen peroxide by color development using an oxidative color-developing agent. By using the method and kit of the present invention, homocysteine in biological samples, in particular, in body fluids such as blood and urine can be detected and quantitatively determined rapidly and simply and with high sensitivity.

26 Claims, 11 Drawing Sheets

OTHER PUBLICATIONS

Jacobsen, Donald W., "Homocysteine and vitamins in cardiovascular disease", *Clinical Chemistry* 44:8(B), 1998, pp. 1833–1843.

Selhub, Jacob et al., "Vitamin Status and Intake as Primary Determinants of Homocysteinemia in an Elderly Population", *JAMA*, Dec. 8, 1993—vol. 270, No. 22, pp. 2693–2698.

Shipchandler, Mohammed T. et al., "Rapid, Fully Automated Measurement of Plasma Homocyst(e)ine with the Abbott IMx® Analyzer", *Clinical Chemistry*, vol. 41, No. 7, 1995, pp. 991–994.

Partial Translation of Seikagakujiten (Biochemistry Dictionary) 3d edition, Tokyo Kagaku Dojin, 1998, p. 182 (4 pp.).

Enzyme Handbook, Asakura Syoten, 1982, p. 529 (3 pp.)—No English translation.

Frieden, Carl et al., "Adenosine Deaminase and Adenylate Deaminase: Comparative Kinetic Studies with Transition State and Ground State Analogue Inhibitors", Biochemistry, *American Chemical Society*, 1980, pp. 5303–5309.

Guranowski, Andrzej et al., "Adenosylhomocysteinase from Yellow Lupin Seeds", *Eur. J. Biochem.* 80, 1977, pp. 517–523.

Chiang, Peter K., "Adenosylhomocysteinase (Bovine)", [Chapter 64], *Methods in Enzymology*, vol. 143, Academic Press, Inc., 1987, pp. 377–383.

Shapiro, Stanley K., "Adenosylmethionine–Homocysteine Transmethylase", ATP–Phosphate Exchange, *Biochim. Biophys. Acta*, vol. 29, 1958, pp. 405–409.

Grue–Sørensen, Gunnar et al., "Diastereospecific, Enzymically Catalysed Transmethylation from S–Methyl–L–methionine to L–Homocysteine, a Naturally Occurring Process", *J. Chem. Soc.*, Perkin Trans. 1, 1984, pp. 1091–1097.

Livesey, Geoffrey et al, "Isolation and Characterization of Leucine Dehydrogenase from *Bacillus subtillis*", [Chapter 36], *Methods in Enzymology*, vol. 166, Academic Press, Inc., 1988, pp. 282–288.

Ikeda et al., "A method for quantitative measuring NAD(P)H", *Rinshokensa* (Clinical Test), vol. 41 No. 9, 1997, pp. 989–993, Partial translation from p. 990, right column, line 5 through p. 991, left column, line 16.

"A recommended method for measuring enzyme activity in human serum—Creatine kinase—", *Rinshokagaku* (Clinical Chemistry), vol. 19 No. 2, 1990, pp. 189–208, Partial translation of p. 195, right column, lines 1 to 14.

Shapiro, Stanley K., "S–Adenosylmethionine: L–Homocysteine S–Methyltransferase[1.1a] (*Saacharomyces cerevisiae*)", *Methods Enzymol.*, 17 Pt.B, Sulfur Amino Acids, 1971, pp. 400–405.

* cited by examiner

METHOD OF MEASURING TOTAL HOMOCYSTEINE

BACKGROUND OF THE INVENTION

1. Field of the Invention

The present invention relates to a method for determining total homocysteine.

2. Description of the Prior Art

Homocysteine, which is one of the metabolic intermediates in methionine metabolism, is reported to have vascular endothelial cytotoxicity and to be one of the risk factors for arteriosclerotic diseases independent from the other risk factors. It also has been evident that in addition to serious hyperhomocysteinemia (homocystinuria) caused by deficiency of homocysteine metabolic enzymes, moderate hyperhomocysteinemia is caused by a decrease in the metabolic enzyme activity due to abnormality of genes, renal insufficiency, aging, smoking, lack of exercise or the like (Jacobsen, Clin. Chem. 44:8(B), 1833–1843, 1998). Furthermore, hyperhomocysteinemia is also reported to be improved by taking vitamin B6, folic acid or the like (JAMA 270: 2693–2698, 1993). Therefore, not only for neonatal mass screening, but also for prevention of adult arteriosclerotic diseases or detection of vitamin deficiency diseases, a simple method for treating a large number of specimens is in demand.

Most of homocysteine in blood (99%) is present in the form of oxidized disulfide compounds (such as complex with protein, homocystine, cysteine-homocysteine) (Jacobsen, Clin. Chem. 44:8(B), 1833–1843, 1998). "Total homocysteine" refers to the total amount of oxidized and reduced homocysteines, and in general, it is necessary to convert homocysteine in a sample to reduced homocysteine by a reducing agent in order to determine the total homocysteine.

High-performance liquid chromatography (HPLC) and immunoassay are usually employed to determine homocysteine. However, the HPLC apparatuses used in high-performance liquid chromatography are not commonly used in the clinical test, and it takes time, labor and cost to operate the apparatuses. In the immunoassay, although apparatuses are automated (Shipchandler, Clin. Chem., 41, 7, 991–994, 1995), determination is performed by combining a process for converting homocysteine to S-adenosyl-L-homocysteine by an enzyme reaction and a process for detecting it by an immunoassay, so that an apparatus used exclusively for this purpose is required.

Determination methods of homocysteine based on an immunoassay are proposed in Japanese Laid-Open Patent Publication (Tokuhyo) No. 9-512634 and (Tokkai) No. 10-114797. In the method disclosed in Japanese Laid-Open Patent Publication No. 9-512634, homocysteine is determined immunologically by chemically modifying the homocysteine to enhance the antigenicity, which requires a large number of processes and is complicated. Japanese Laid-Open Patent Publication No. 10-114797 discloses a method for determining homocysteine, but this method directly determines only the homocysteine bound to albumin, and does not determine the total amount of homocysteine. In this method, only about 70% of the entire homocysteine can be determined.

On the other hand, biochemical determination methods of homocysteine are disclosed in Japanese Patent No. 2870704, U.S. Pat. Nos. 5,998,191 and 5,885,767. The method disclosed in Japanese Patent No. 2870704 is characterized by allowing homocysteine in a sample that has been treated with a reducing agent to be in contact with adenosine and S-adenosyl-L-homocysteine hydrolase and evaluating the amount of adenosine in the residual mixture. However, in this method, an inhibitor of the S-adenosyl-L-homocysteine hydrolase is not used, and therefore it is necessary to perform determination in kinetic mode. Furthermore, this method has the problem that produced hydrogen peroxide cannot be led to a commonly used oxidative color-developing agent in the presence of a reducing agent that is used for a reduction process, which is an essential process for determining the total homocysteine. Therefore, an automatic analysis apparatus for general purposes cannot be used. However, these patent specifications fail to disclose any method to avoid these problems.

The methods disclosed in Japanese Laid-Open Patent Publication (Tokuhyo) No. 2000-502262, U.S. Pat. Nos. 5,998,191 and 5,885,767 are characterized by reacting homocysteine with homocysteine desulfurase, homocysteinase, or methionine-γ-lyase to detect the produced hydrogen sulfide, ammonia, or 2-oxobutyric acid. However, these methods have problems such as: requiring a large number of processes; employing a lead ion, which is a harmful heavy metal, for the detection of the hydrogen sulfide; and being affected by cysteine and methionine, which are structural analogs to homocysteine and contained in a biological sample in a larger amount than that of homocysteine.

Thus, the conventional methods of determining homocysteine have problems such as requiring a special apparatus and complicated operation and having insufficient sensitivity and specificity, so that a method for determining a trace concentration of homocysteine rapidly, simply and with high sensitivity has not been established yet.

SUMMARY OF THE INVENTION

The present invention provides a novel method for determining homocysteine contained in a biological sample or the like rapidly, simply and with high sensitivity, and a kit for use in this determination method.

The inventors of the present invention succeeded in detecting or determining homocysteine by (i) oxidizing the residual homocysteine cosubstrate, the produced homocysteine-converting enzyme product or an enzyme reaction product thereof in the presence of an SH reagent to produce hydrogen peroxide and detecting or determining the produced hydrogen peroxide by color development using an oxidative color-developing agent or (ii) reacting the residual homocysteine cosubstrate, the produced homocysteine-converting enzyme product or an enzyme reaction product thereof with a D-amino acid converting enzyme to produce an oxo acid and/or ammonia and detecting or determining the produced oxo acid and/or ammonia. With the method for determining homocysteine of the present invention, homocysteine in a biological sample, in particular in body fluids such as blood and urine can be detected and determined rapidly and simply.

The present invention is directed to a method for detecting or determining homocysteine in a sample including:

(a) reducing the homocysteine in the sample by a thiol compound, (b) reacting the reduced homocysteine with a homocysteine-converting enzyme and a homocysteine cosubstrate, thereby producing a homocysteine-converting enzyme product, and (c) detecting or determining the residual homocysteine cosubstrate, the produced homocysteine-converting enzyme product or an enzyme reaction product thereof by: (i) oxidizing the residual homocysteine cosubstrate, the produced homocysteine-converting enzyme product or an enzyme reaction product thereof in the presence of an SH reagent to produce hydrogen peroxide and detecting or determining the produced hydrogen peroxide by color development using an oxidative color-developing agent or (ii) reacting the residual homocysteine cosubstrate, the produced homocysteine-converting enzyme product or an enzyme reaction product thereof with a D-amino acid converting enzyme to produce an oxo acid and/or ammonia and detecting or determining the produced oxo acid and/or ammonia.

In one preferable embodiment, the homocysteine-converting enzyme in the step (b) is S-adenosyl-L-homocysteine hydrolase, and the homocysteine cosubstrate in the steps (b) and (c) is adenosine.

In one preferable embodiment, the step (c) of detecting or determining the adenosine is a step of detecting or determining the adenosine by reacting the adenosine with adenosine deaminase, phosphoric acid, purine nucleoside phosphorylase, and xanthine oxidase to produce hydrogen peroxide and detecting or determining the produced hydrogen peroxide by color development using peroxidase and an oxidative color-developing agent.

In a more preferable embodiment, the step (c) includes further reacting the adenosine with uricase.

In another more preferable embodiment, the homocysteine-converting enzyme in the step (b) is a methyltransferase using homocysteine as a methyl acceptor, and the homocysteine cosubstrate in the steps (b) and (c) is a methyl donor.

In one preferable embodiment, the methyltransferase is homocysteine methyltransferase, and the methyl donor is D-methionine methyl sulfonium.

In a more preferable embodiment, in the step (c), the homocysteine-converting enzyme product is D-methionine, and the D-methionine is determined by reacting it with a D-amino acid converting enzyme.

In a more preferable embodiment, the D-amino acid converting enzyme is D-amino acid oxidase.

In one preferable embodiment, in the step (c), the hydrogen peroxide produced by a reaction with the D-amino acid oxidase is detected or determined by color development using peroxidase and an oxidative color-developing agent.

In one preferable embodiment, the SH reagent is a maleimide derivative.

In another preferable embodiment, in the step (c), a decrease in NAD(P)H or an increase in NAD(P) is detected or determined by reacting the produced oxo acid and/or ammonia with dehydrogenase using NAD(P)H as a coenzyme.

In one preferable embodiment, in the step (c), the oxo acid and/or ammonia produced by a reaction with the D-amino acid oxidase is detected or determined.

In one preferable embodiment, in the step (c), a decrease in NAD(P)H or an increase in NAD(P) is detected or determined by reacting the produced oxo acid and/or ammonia produced by a reaction with the D-amino acid oxidase with dehydrogenase using NAD(P)H as a coenzyme.

In one preferable embodiment, the dehydrogenase is leucine dehydrogenase, and a decrease in NAD(P)H is detected or determined by reacting the produced oxo acid with the leucine dehydrogenase in the presence of ammonia and NAD(P)H.

In one preferable embodiment, the dehydrogenase is lactate dehydrogenase, and a decrease in NAD(P)H is detected or determined by reacting the produced oxo acid with the lactate dehydrogenase in the presence of NAD(P)H.

In one preferable embodiment, the dehydrogenase is glutamate dehydrogenase, and a decrease in NAD(P)H is detected or determined by reacting the produced ammonia with the glutamate dehydrogenase in the presence of 2-oxoglutaric acid and NAD(P)H.

In a more preferable embodiment, the dehydrogenase is lactate dehydrogenase and glutamate dehydrogenase, and a decrease in NAD(P)H is detected or determined by a reaction with the lactate dehydrogenase and the glutamate dehydrogenase in the presence of 2-oxoglutaric acid and NAD(P)H.

In a more preferable embodiment, the steps (a) and (b) are performed at the same time.

The present invention also is directed to a reagent kit for homocysteine determination comprising a thiol compound, a homocysteine-converting enzyme, a homocysteine cosubstrate, an SH reagent, and an oxidative color-developing agent.

In one preferable embodiment, the SH reagent is contained in another container from one for the thiol compound, the homocysteine-converting enzyme and the homocysteine cosubstrate.

In one preferable embodiment, the homocysteine-converting enzyme is contained in another container from one for the homocysteine cosubstrate.

In a more preferable embodiment, the homocysteine-converting enzyme is S-adenosyl-L-homocysteine hydrolase, and the homocysteine cosubstrate is adenosine.

In an even more preferable embodiment, the kit further includes adenosine deaminase, phosphoric acid, purine nucleoside phosphorylase, xanthine oxidase, and peroxidase.

In another preferable embodiment, the adenosine deaminase is contained in another container from one for the thiol compound, the S-adenosyl-L-homocysteine hydrolase and the adenosine.

In one preferable embodiment, the kit further includes uricase.

The present invention also is directed to a reagent kit for homocysteine determination comprising a thiol compound, a homocysteine-converting enzyme, a homocysteine cosubstrate, and a D-amino acid converting enzyme.

In one preferable embodiment, the kit further includes NAD(P)H, dehydrogenase using NAD(P)H as a coenzyme, and an ammonium salt or 2-oxo acid as its cosubstrate.

In a more preferable embodiment, the dehydrogenase is leucine dehydrogenase, and the cosubstrate of the enzyme is an ammonium salt.

In another more preferable embodiment, the dehydrogenase is glutamate dehydrogenase, and the cosubstrate of the enzyme is a 2-oxoglutaric acid.

In one preferable embodiment, the dehydrogenase is lactate dehydrogenase.

In another preferable embodiment, the homocysteine-converting enzyme is a methyltransferase using homocysteine as a methyl acceptor, and the homocysteine cosubstrate is a methyl donor.

In one preferable embodiment, the methyltransferase is homocysteine methyltransferase, and the methyl donor is D-methionine methyl sulfonium.

In one preferable embodiment, the D-amino acid converting enzyme is D-amino acid oxidase.

In one preferable embodiment, the D-amino acid oxidase is contained in another container from one for the thiol compound and the homocysteine methyltransferase.

In one preferable embodiment, the SH reagent is a maleimide derivative.

DETAILED DESCRIPTION OF THE INVENTION

The method of the present invention is characterized by reacting homocysteine in a sample that has been reduced by a thiol compound with a homocysteine-converting enzyme and a homocysteine cosubstrate, and then determining a homocysteine-converting enzyme product or a residual homocysteine cosubstrate in the presence of an SH reagent. Preferably, S-adenosyl-L-homocysteine hydrolase and adenosine are used as the homocysteine-converting enzyme and the homocysteine cosubstrate, and the residual adenosine is determined by using an oxidative color-developing agent in the presence of an SH reagent. In a more preferable embodiment, the method of the present invention includes a process of converting homocysteine in a test sample to a reduced homocysteine by a treatment with a thiol compound, and simultaneously reacting the homocysteine with S-adenosyl-L-homocysteine hydrolase and adenosine so as to produce S-adenosyl-L-homocysteine (hereinafter, referred to as a first process) and a process of determining the residual adenosine by using an oxidative color-developing agent in the presence of an SH reagent (hereinafter, referred to as a second process).

Alternatively, the method of the present invention is characterized by reacting homocysteine in a sample with a methyltransferase in the presence of a methyl donor and then determining the produced D-amino acid derivative or D-amino acid analog. Examples of the methyl donor include D-methionine methyl sulfonium, S-adenosyl-D-methionine, and D-ethionine methyl sulfonium. Preferably, D-methionine methyl sulfonium can be used.

The determination principles of the present invention will be described with reference to FIG. 1 in the case (A) where S-adenosyl-L-homocysteine hydrolase and adenosine are used as the homocysteine-converting enzyme and the homocysteine cosubstrate, and with reference to FIG. 2 in the case (B) where a methyltransferase and D-methionine methyl sulfonium are used as the homocysteine-converting enzyme and the homocysteine cosubstrate.

(A) Determination Principle when S-adenosyl-L-homocysteine Hydrolase and Adenosine are used (SAHase Method)

Figure 1:
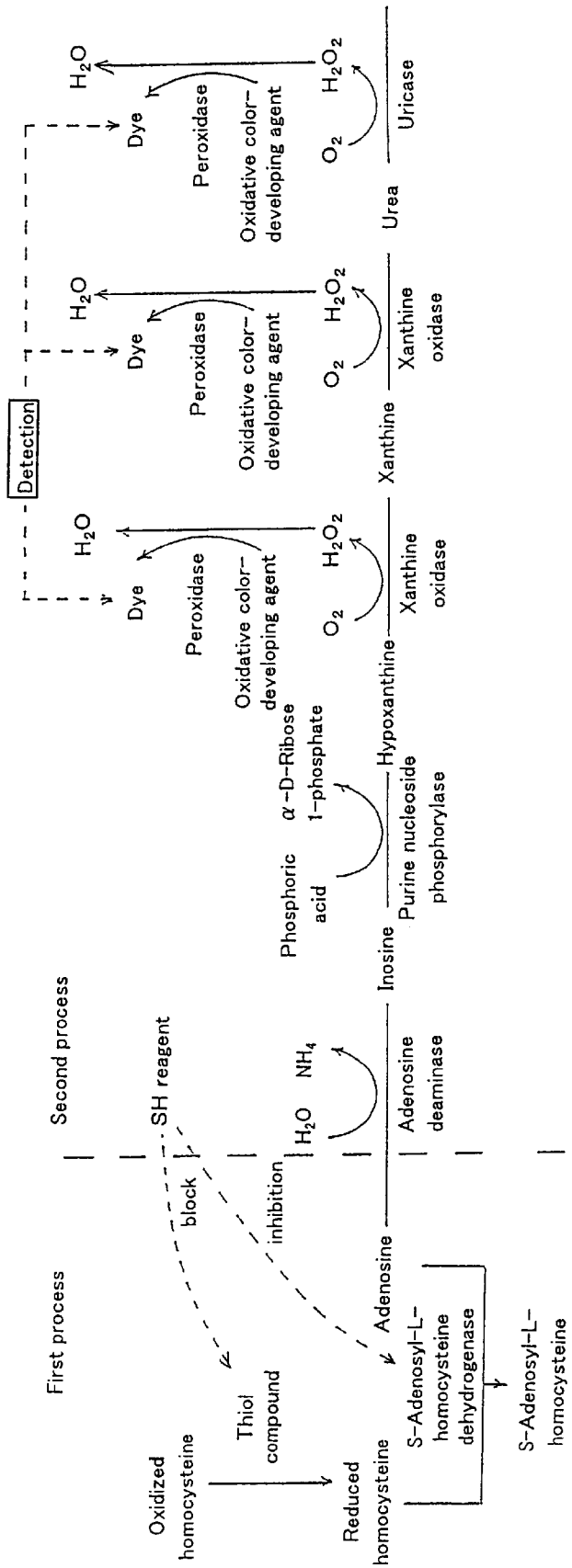
FIG. 1 is a schematic diagram of the reaction when S-adenosyl-L-homocysteine hydrolase and adenosine are used as a homocysteine-converting enzyme and a homocysteine cosubstrate.

In the first process of FIG. 1, the reduced homocysteine is reacted with S-adenosyl-L-homocysteine hydrolase and adenosine. In this process, the equilibrium of the enzyme reaction is tend to the synthesis of S-adenosyl-L-homocysteine, and the adenosine is consumed together with the homocysteine. Then, in the second process, the residual adenosine is reacted with adenosine deaminase, purine nucleoside phosphorylase, xanthine oxidase or the like to produce hydrogen peroxide, and a color is developed by peroxidase and an oxidative color-development agent for determination. As seen from FIG. 1, in the first process, the amount of the adenosine consumed is proportional to the amount of the homocysteine. In the second process, as described below in detail, an SH reagent is added as an inhibitor of the S-adenosyl-L-homocysteine hydrolase and a blocking agent of the thiol compound, so that the determination can be performed with high sensitivity. Furthermore, in the second process, uricase is added so that the production of hydrogen peroxide increases and thus the determination can be performed with even higher sensitivity.

Examples employing an SH reagent to determine homocysteine are described in Japanese Laid-Open Patent Publication (Tokuhyo) No. 9-512634 and U.S. Pat. No. 6,020,206. As described above, the former is a method including chemically modifying homocysteine to enhance the immunogenicity and detecting it immunologically, and in the method an SH compound is used as the modifier. The latter is a method including converting homocysteine to homocysteine thiolactone to protect the thiol group, removing other compounds having a thiol group, such as cysteine contained in the sample, with an SH reagent, opening the ring of the thiolactone, and determining the homocysteine. Both of the methods have completely different determination principles from that of the present invention, and the SH reagent is used for a different purpose from that of the present invention. Furthermore, for determination of free fatty acids, there are some examples where an SH reagent is used to prevent a cosubstrate CoA from interfering with the determination by using an oxidative color-developing agent (Japanese Laid-Open Patent Publication (Tokkai) Nos. 55-64800 and 57-8797). However, the determination is performed regarding different items, so that it cannot be predicted whether or not the SH reagent is effective in the present invention.

Examples of the SH reagent include an oxidizing agent such as the Ellman's reagent, a mercaptide forming agent such as p-mercuribenzoic acid, and an alkylating agent such as iodoacetic acid and N-ethylmaleimide, as described in Seikagakujiten (Biochemical Dictionary) (third edition, p. 182, Tokyo Kagaku Dojin, 1998). Preferably, an alkylating agent, and more preferably a maleimide compound, and most preferably, N-ethylmaleimide can be used.

Any sample can be used as the test sample to be subjected to the method of the present invention, as long as it is believed to contain homocysteine. The homocysteine can be present in the form of, not only reduced homocysteine, but also oxidized homocysteine that is bound to another molecule by a disulfide bond such as a complex with protein, a homocysteine dimer and a homocysteine-cysteine dimer. For example, serum, plasma, blood, urine and a dilution thereof can be used.

The thiol compound used in the method of the present invention is not particularly limited, and includes, for example, dithiothreitol, mercaptoethanol, N-acetylcysteine, dithioerythritol, and thioglycolic acid. Any concentration can be employed as the concentration of the thiol compound, as long as it allows oxidized homocysteine to be converted to reduced homocysteine. Preferably, the concentration is 0.1 mM or more in terms of a thiol group, and more preferably 1 mM or more.

Following or at the same time as the reduction process by the use of the thiol compound, in the first process of the present invention, a homocysteine-converting enzyme and a homocysteine cosubstrate, preferably, S-adenosyl-L-homocysteine hydrolase and adenosine are reacted with the homocysteine to produce S-adenosyl-L-homocysteine.

The amount of the residual homocysteine cosubstrate, preferably the amount of the adenosine, depends on the amount of the homocysteine to be determined, as evident from the determination principle of the method of the present invention. More specifically, in a reaction in which water or a buffer is used as a sample, that is, a reaction in which homocysteine is not contained, the amount of the adenosine is set to a value that allows the absorbance to change from 0.0005 to 4, preferably 0.001 to 2, even more preferably 0.005 to 1, from before the end of the first process to the end of the second process.

The S-adenosyl-L-homocysteine hydrolase is an enzyme for catalyzing both a synthesis reaction and a hydrolysis reaction, which is the reverse reaction of the synthesis reaction, and the equilibrium of the reaction lies significantly to the synthesis direction, but since the product can be metabolized rapidly in an organism, this enzyme serves as a hydrolysis system (Enzyme Handbook, p. 529, Asakura Syoten (1982)). This enzyme is isolated from various sources such as rabbits, lupine seeds, bovines, rats, yeasts, and bacteria. There is no particular limitation regarding the source. Enzymes obtained by gene recombination also can be used. The concentration employed is preferably 0.01 U/mL to 100 U/mL, more preferably 0.1 U/mL to 20 U/mL.

It is preferable that this enzyme specimen is minimized to contain an enzyme that can act on adenosine, such as adenosine deaminase. However, some commercially available specimens contain adenosine deaminase in a very small content. In this case, by purifying the enzyme, the effect of adenosine deaminase can be avoided. Alternatively, the effect of the contamination of the adenosine deaminase can be avoided by determining the difference between the reactivity of the reagent containing the specimen of the enzyme (S-adenosyl-L-homocysteine hydrolase) and that of the reagent not containing the same.

Furthermore, in order to suppress the activity of the contaminated adenosine deaminase, an inhibitor can be used. Any inhibitor can be used, as long as it does not intensely act on the S-adenosyl-L-homocysteine hydrolase. However, in view of the enzyme reaction in the second process as described below, coformycin, deoxycoformycin, 1,6-dihydro-6-hydroxymethylpurine ribotide (Biochemistry, 19:223, 5303–5309, 1980) and the like, which are believed to have particularly little effect on the initial rate of the adenosine deaminase reaction, are preferable. When an inhibitor is used, it is preferable to use an excessive amount of adenosine deaminase in the second process.

In the following second process, the homocysteine-converting enzyme product or the residual homocysteine cosubstrate is determined. Preferably, first, the residual adenosine is converted to inosine by the action of adenosine deaminase. Thus, the substrate for the S-adenosyl-L-homocysteine hydrolase reaction in the first process decreases, that is, the product of the reverse reaction thereof decreases, so that the equilibrium of the reaction is directed to hydrolysis. If the activity of the S-adenosyl-L-homocysteine hydrolase remains in this process, the reverse reaction of the first process, that is, the S-adenosyl-L-homocysteine hydrolysis reaction occurs at the same time, which eventually leads to lower the sensitivity for homocysteine determination. Therefore, in order to prevent this reaction, it is preferable to add an inhibitor of the S-adenosyl-L-homocysteine hydrolase. As inhibitors of this enzyme, the SH reagent (Eur. J. Biochem. 80, 517–523, 1977) and some adenosine derivatives (Methods in Enzymology 143, 377–383, 1987) are known. In the method of the present invention, any inhibitor can be used, as long as it does not cause a large impediment in other reaction systems. The inhibitors can be used in combination.

The produced inosine produces hydrogen peroxide by being brought into contact with phosphoric acid, purine nucleoside phosphorylase, xanthine oxidase, and, if necessary, uricase so that a usual oxidative color-developing agent can develop a color with peroxidase. This method is generally employed in the field of clinical chemistry, but the color development is significantly interfered by the reductive action of the thiol compound used in the first process. Therefore, it is essential to add an SH reagent, which is a blocking agent of the thiol compound, in the second process. Thus, the addition of an SH reagent in the second process serves to prevent the S-adenosyl-L-homocysteine hydrolase used in the first process from catalyzing the reverse reaction (hydrolysis reaction) in the second process, and also serves to prevent the thiol compound from interfering with the color development of the oxidative color-developing agent. Any concentration can be employed as the concentration of the SH reagent in the second process, as long as it can block the thiol group of the thiol compound used for a reduction treatment of the sample from interfering with the quantitative determination by the use of the oxidative color-developing agent. The concentration can be preferably 0.1 mM to 100 mM. More preferably it is 1 mM to 30 mM. It is preferable to use an excessively larger amount of the SH reagent than that of the thiol compound used, in order to exhibit the effect of inhibiting the S-adenosyl-L-homocysteine hydrolase.

As the oxidative color-developing agent, various Trinder reagents can be used in combination with a coupler reagent. This method may be called the Trinder method, and is commonly used in the field of the clinical chemical analysis. Although the detailed description is omitted herein, it is preferable to use 4-aminoantipyrine as the coupler reagent and to use ADOS [N-ethyl-N-(2-hydroxy-3-sulfopropyl)-3-methoxyaniline], DAOS [N-ethyl-N-(2-hydroxy-3-sulfopropyl)-3,5-dimethoxyaniline], HDAOS [N-(2-hydroxy-3-sulfopropyl)-3,5-dimethoxyaniline], MAOS [N-ethyl-N-(2-hydroxy-3-sulfopropyl)-3,5-dimethylaniline], TOOS [N-ethyl-N-(2-hydroxy-3-sulfopropyl)-3-methylaniline] or the like as the Trinder reagent. Furthermore, leuco-type color-developing agent such as o-tolidine, o-dianisidine, DA-67 [10-(carboxymethylaminocarbonyl)-3,7-bis(dimethylamino) phenothiazine sodium, manufactured by Wako Pure Chemical Industries, Ltd.], and TPM-PS [N,N,N',N',N'',N''-hexa(3-sulfopropyl)-4,4',4''-triaminotriphenylmethane hexasodium salt, Dojin Kagaku Kenkyusho], which do not require the coupler reagent, can be used as well. In particular, DA-67 and TPM-PS have a mole absorption coefficient larger than that of the Trinder reagent, so that the determination can be performed with higher sensitivity.

A reaction intermediate after inosine in the second process may be contained in the sample, so that for the purpose of avoiding the effect on the value to be obtained, hydrogen peroxide can be produced by using purine nucleoside phosphorylase and phosphoric acid, which are cosubstrates thereof, and xanthine oxidase, and, if necessary, uricase in the first process. The produced hydrogen peroxide disappears by the action of a reducing agent contained in the first process, but it is preferable to further degrade the produced hydrogen peroxide into water and oxygen by catalase or to produce a colorless complex by reacting the produced hydrogen peroxide with one of the Trinder reagent or the coupler reagent using peroxidase.

In the method of the present invention, it is possible to determine homocysteine by using only a reagent containing the S-adenosyl-L-homocysteine hydrolase described above. However, in order to further enhance the determination precision, by determining a reagent not containing this enzyme at the same time, the effect of the adenosine contained in the sample can be avoided. More specifically, the value obtained by the determination with a reagent not containing the S-adenosyl-L-homocysteine hydrolase indicates the total amount (total adenosine) of the amount of the adenosine previously contained in the reagent and the amount of the adenosine contained in the sample. On the other hand, the reagent containing the S-adenosyl-L-homocysteine hydrolase indicates the amount obtained by subtracting the amount of the adenosine consumed in the first process from the total amount of the adenosine described above. The difference between the thus obtained two values indicates the amount of the consumed adenosine, that is, the amount of homocysteine.

(B) Determination Principle when a Methyltransferase and D-methionine Methyl Sulfonium are used (Methyltransferase Method (Hereinafter, Referred to as MTase Method))

Next, the determination principle of the case where a methyltransferase using homocysteine as a methyl acceptor and D-methionine methyl sulfonium, which is a methyl donor, are used will be described with reference to FIG. 2. In other words, in this case, the homocysteine in a sample is reacted with a methyltransferase and D-methionine methyl sulfonium, and then the produced D-methionine is determined.

(1) MTase Method I

Any methyltransferase can be used, as long as it reacts with D-methionine methyl sulfonium and L-homocysteine and catalyzes the production of D-methionine and L-methionine. Examples of the methyltransferase include homocysteine methyltransferase [EC 2.1.1.10], 5-methyltetrahydrofolic acid-homocysteine S-methyltransferase [EC 2.1.1.13], 5-methyltetrahydropteroyltriglutamic acid-homocysteine S-methyltransferase [EC 2.1.1.14]. Preferably, homocysteine methyltransferase [EC 2.1.1.10] can be used. The phylogenetic name of homocysteine methyltransferase is S-adenosyl-L-methionine: L-homocysteine S-methyltransferase, and this enzyme produces L-methionine and S-adenosyl-L-homocysteine, using L-homocysteine, which is a methyl acceptor, and S-adenosyl-L-methionine, which is a methyl donor, as the substrates (Enzyme handbook, Asakura Syoten, 1982). Furthermore, S. K. Shapiro has reported that this enzyme also utilizes S-methyl-L-methionine (L-methionine methyl sulfonium) or S-adenosyl-D-methionine as the methyl donor (Biochim. Biophys. Acta, 29, 405–409, 1958).

This report also confirmed from the results of labeling experiments with a radioisotope that methionine is produced by the methyl group of S-adenosylmethionine being transferred to homocysteine, and not by the bond between ribose and a sulfur atom of S-adenosyl methionine being opened. Therefore, when S-adenosyl-L-methionine is used as the methyl donor, L-methionine and S-adenosyl-L-homocysteine is produced. When L-methionine methyl sulfonium is used as the methyl donor, two L-methionine molecules are produced. When S-adenosyl-D-methionine is used as the methyl donor, L-methionine and S-adenosyl-D-homocysteine is produced. In all the cases, L-methionine is produced, so that the amount of the homocysteine can be quantitatively determined by determining the L-methionine.

However, in general, L-methionine is contained in a biological sample in a larger amount than that of homocysteine (3 to 5 times larger in plasma), so that it is necessary to remove L-methionine previously in a manner that does not affect homocysteine and to determine specifically the L-methionine that is produced by a homocysteine methyltransferase reaction, which is a complicated operation, and therefore this method is not preferable. On the other hand, G. Grue-Sorensen et al. have reported that homocysteine methyltransferase produces D-methionine by using D-methionine methyl sulfonium as the methyl donor (J. Chem. Soc. Perkin Trans. I 1091–7 (1984)), although the specificity is low. For this reason, in the method of the present invention, utilizing this reaction, D-methionine, which is not substantially present in a biological sample, is produced, and then the D-methionine is determined so as to quantitatively determine homocysteine specifically.

Homocysteine methyltransferase derived from any sources can be used as the homocysteine methyltransferase for the present invention, as long as it uses D-methionine methyl sulfonium as the methyl donor. For example, enzymes derived from bacteria, yeasts, rats or the like can be used.

There is no particular limitation regarding the method for quantitatively determining D-methionine, but it is preferable to determine it enzymatically with a D-amino acid converting enzyme. More preferably, D-amino acid oxidase [EC 1.4.3.3] is used. The inventors of the present invention have unexpectedly made it evident that D-methionine methyl sulfonium, which is a D-amino acid, substantially cannot serve as a substrate of D-amino acid oxidase. Thus, if the D-amino acid converting enzyme does not react with D-methionine methyl sulfonium, or even though this enzyme reacts therewith, if the enzyme has a sufficiently lower reactivity than that with respect to D-methionine, the produced D-methionine can be determined without removing the D-methionine methyl sulfonium that remains after the reaction with homocysteine methyltransferase from the reaction system. In addition to D-amino acid oxidase, D-amino acid acetyltransferase [EC 2.3.1.36], D-amino acid dehydrogenase [EC 1.4.99.1], and the like, which have the similar properties, can be used (FIG. 2).

Figure 2:
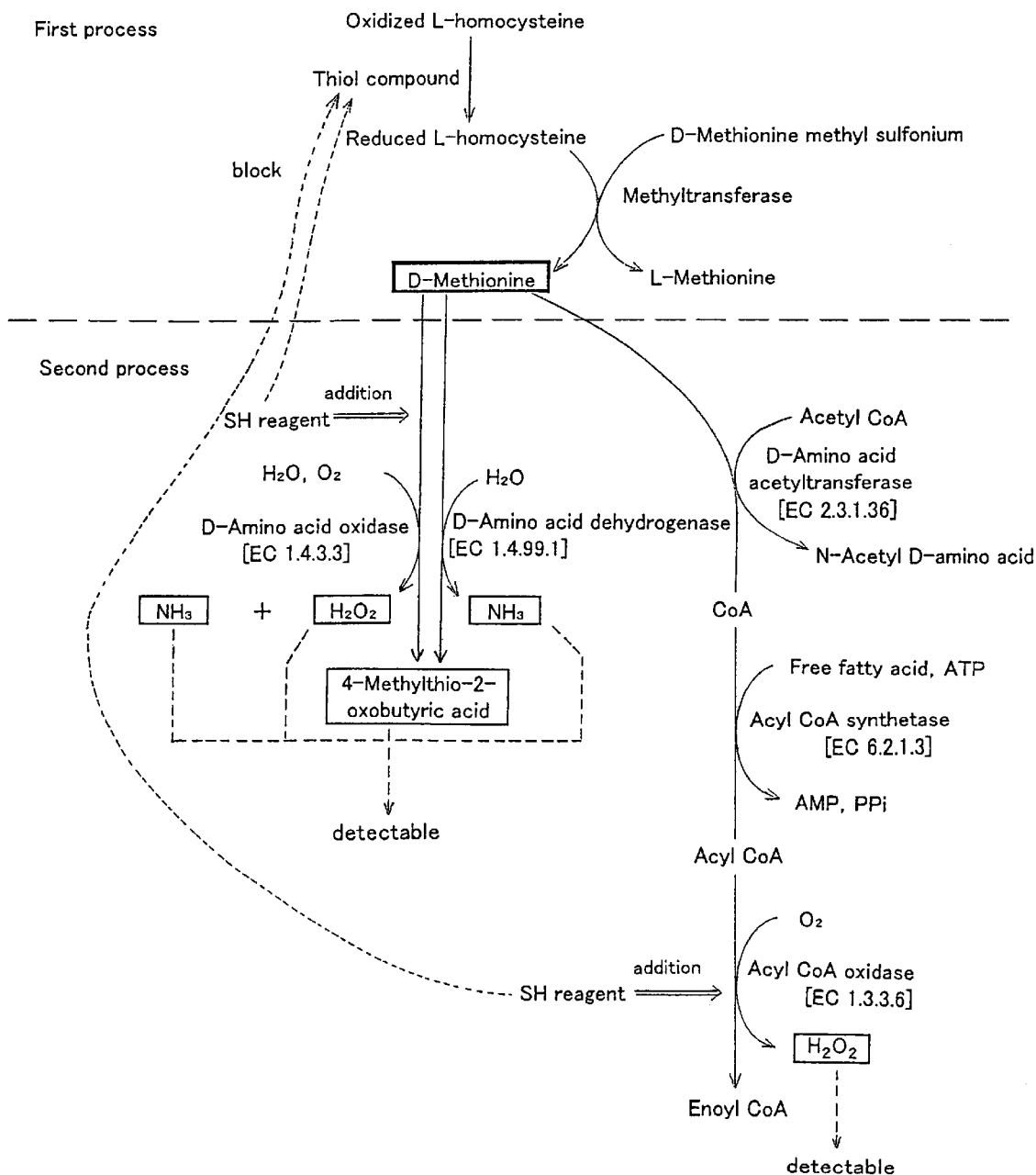
FIG. 2 is a schematic diagram of the reaction when homocysteine transferase and D-methionine methyl sulfonium are used as a homocysteine-converting enzyme and a homocysteine cosubstrate.

As shown in FIG. 2, when D-methionine is reacted with D-amino acid oxidase, hydrogen peroxide is produced. This hydrogen peroxide is led to an oxidative color-developing agent commonly used in the presence of an SH reagent so as to be determined colorimetrically, as described above. Furthermore, when D-methionine is reacted with D-amino acid acetyltransferase, the produced coenzyme A is led to hydrogen peroxide by acyl-coenzyme A synthetase [EC 6.2.1.3] and an acyl-coenzyme A oxidase [EC 1.3.3.6], and this hydrogen peroxide can be quantitatively determined in the same manner.

(2) MTase Method II

When D-methionine is reacted with D-amino acid oxidase or D-amino acid dehydrogenase, ammonia and 4-methylthio-2-oxobutyric acid are produced. Homocysteine can be quantitatively determined by determining these products.

Ammonia can be quantitatively determined by reacting the ammonia with reduced nicotinamide adenine dinucleotide (NADH), reduced nicotinamide adenine dinucleotide phosphate (NADPH) or derivatives thereof (hereinafter, referred to as NAD(P)H in this specification), 2-oxoglutaric acid and glutamate dehydrogenase ([EC 1.4.1.2], [EC 1.4.1.3], or [EC 1.4.1.4]), and determining a decrease in NAD(P)H by measuring the absorbance change at 340 nm. Alternatively, an increase in NAD, or NADP or derivatives thereof (hereinafter, referred to as NAD(P) in this specification) can be determined. Examples of the derivatives of NAD(P)H include thio NAD(P)H, and 3-acetylpyridine adenine dinucleotide (or 3-acetylpyridine dinucleotide phosphate). For the determination of ammonia, in addition to the glutamate dehydrogenase as described above, any dehydrogenase can be used, as long as it can catalyze a reductive amination reaction utilizing ammonia with NAD(P)H as a coenzyme. For example, leucine dehydrogenase ([EC 1.4.1.9]), alanine dehydrogenase ([EC 1.4.1.1]), serine dehydrogenase ([EC 1.4.1.7]), valine dehydrogenase ([EC 1.4.1.8]), and glycine dehydrogenase ([EC 1.4.1.10]) can be used. As a cosubstrate of these dehydrogenases, an ammonium salt, a 2-oxo acid or the like can be used. Examples of the 2-oxo acid include pyruvic acid, 2-oxobutyric acid, 2-oxoisocaproic acid, 2-oxoisovaleric acid, 2-oxovaleric acid, 2-oxocaproic acid, glyoxylic acid, and hydroxypyruvic acid, in addition to 2-oxoglutaric acid as described above.

Ammonia can be quantitatively determined by utilizing a Nessler's reagent, a pH indicator, an electrode method or other methods.

4-Methylthio-2-oxobutyric acid can be quantitatively determined by reacting the 4-methylthio-2-oxobutyric acid with NADH, ammonia and leucine dehydrogenase [EC 1.4.1.9], and determining, for example, a decrease in NADH by measuring the absorbance change at 340 nm as in the case of ammonia. It is known that 4-methylthio-2-oxobutyric acid serves as a substrate of leucine dehydrogenase (G. Livesey et al. Methods in Enzymology, 166, 282–288, 1988). For the determination of 4-methylthio-2-oxobutyric acid, in addition to the leucine dehydrogenase as described above, any dehydrogenase can be used, as long as it can reduce 4-methylthio-2-oxobutyric acid. For example, lactate dehydrogenase ([EC 1.1.1.27]) can be used.

It is known that the method for leading 4-methylthio-2-oxobutyric acid or ammonia to a system employed for quantitative determination by the absorbance change at 340 nm of NAD(P)H is unlikely to be affected by a reducing agent. Therefore, there is no need of using an SH reagent (Ikeda et al. Rinshokensa (Clinical test), 41, 989–993, 1997). An example of leading them to an NAD(P)H quantitative determination system in the presence of a reducing agent is a determination method of creatine kinase in blood (Rinshokagaku(Clinical Chemistry), 19, 189–208, 1990).

In the determination system in which ammonia or 4-methylthio-2-oxobutyric acid is produced by D-amino acid oxidase, it is possible to remove hydrogen peroxide, which is one of the products, by the use of catalase to avoid the effect thereof.

The method of the present invention can be employed manually or by automatic analysis. For example, when a conventional automatic analysis apparatus for a two reagent system is used, the method is divided into the first process of performing the homocysteine methyltransferase reaction and the second process of detecting D-methionine, so as to determine homocysteine in a biological sample easily.

In the quantitative determination of homocysteine by the method of the present invention, the accuracy depends on D-amino acid in the sample, but the amount of D-amino acid in a biological sample is very small. However, it has been reported that the amount of D-amino acid can be increased in a certain kind of disease. Therefore, in order to avoid the effect of D-amino acids, determination is performed with a reagent prepared in the same manner except that it does not contain homocysteine methyltransferase, and the result is subtracted from the value obtained by determination in a sample contained this enzyme so that the amount of homocysteine can be determined accurately.

When the absorbance of NADH is detected, first, a reagent for a reductive reaction and the second process is added to a sample to cause a reaction, and then a reagent containing homocysteine methyltransferase for the first process is added thereto to cause a reaction. Then, the difference in the absorbance at the end of each reaction is obtained, which makes it possible to quantitatively determine homocysteine without any effect of endogenous substances such as D-amino acid.

Moreover, the present invention provides a kit for determining homocysteine in a sample comprising (a) a thiol compound for reducing homocysteine, (b) a homocysteine-converting enzyme and a homocysteine cosubstrate for reaction with the reduced homocysteine (first process), and (c) (i) an SH reagent and an oxidative color-developing agent or (ii) dehydrogenase using NAD(P)H as a coenzyme and a cosubstrate or a color-developing agent in accordance with the properties of the dehydrogenase for determination of the residual homocysteine cosubstrate or the produced homocysteine-converting enzyme product (second process). In order to perform the reduction process and the first process at the same time, (a) and (b) can be contained together. In particular, when (c) (ii) is used, (a), (b), and (c) can be contained together. As in the case of (A) described above, for the purpose of avoiding the effect of reaction intermediates derived from inosine contained in a sample on the determined value, purine nucleoside phosphorylase, phosphoric acid, xanthine oxidase, catalase, and, if necessary, uricase can be contained in the reagent for the first process. Furthermore, instead of catalase, or in addition to catalase, peroxidase and one of a Trinder reagent or a coupler reagent can be contained.

EXAMPLES

Example 1

Effect of N-ethylmaleimide on Adenosine Deaminase Derived from Bovine Small Intestine and Inosine Determination System Enzyme The effect on the second process in which N-ethylmaleimide (NEM) was used as the SH reagent was examined.

First, 100 mM of phosphate buffer (pH7.4), 1 mM of adenosine, 0.4 U/mL of purine nucleoside phosphorylase (manufactured by Toyobo Co., Ltd.), 3 U/mL of xanthine oxidase (manufactured by Toyobo Co., Ltd.), 11 U/mL of peroxidase (manufactured by Toyobo Co., Ltd.), 1 mM of 4-aminoantipyrine, and 1 mM of N-ethyl-N-(2-hydroxy-3-sulfopropyl)-3-methylaniline (TOOS) were mixed and incubated at 37° C. for 5 minutes. Then, 0.001 U/mL of adenosine deaminase derived from small intestine (manufactured by Sigma-Aldrich Corp.) were added thereto, and the absorbance change at 540 nm was detected by using a spectrophotometer (UV-2200 manufactured by Shimadzu Corporation). The change of absorbance in a linear portion was 0.0676 per minute. Then, 1 mM of N-ethylmaleimide was added and detection was performed in the same manner. The absorbance change was 0.0656 per minute. Consequently, it became evident that N-ethylmaleimide (NEM) hardly affected the determination system of adenosine deaminase derived from bovine small intestine and inosine.

Example 2

Effect of N-ethylmaleimide (NEM) on Adenosine Deaminase Derived from Bovine Pancreas The examination was performed in the same manner as in Example 1 except that the adenosine deaminase derived from bovine small intestine (Sigma-Aldrich Corp.) was replaced by adenosine deaminase derived from bovine pancreas (Sigma-Aldrich Corp.). The results were that the absorbance change for one minute before adding N-ethylmaleimide was 0.0751, whereas it was 0.0721 after the addition. Consequently, it became evident that N-ethylmaleimide (NEM) also hardly affected the adenosine deaminase derived from bovine pancreas.

Example 3

Interference of Color Development by a Reducing Agent in a Homocysteine Determination System by the Use of an Oxidative Color-Developing Agent and the Prevention Thereof by an SH Reagent Determination was performed by using a Hitachi 7170 automatic analysis apparatus (manufactured by Hitachi, Ltd.) at a reaction temperature of 37° C., a dominant wavelength of 546 nm, and a secondary wavelength of 700 nm. First, 180 µL of a reagent 1 containing 100 mM of phosphate buffer (pH7.4), 0.009 mM of adenosine, 0.8 U/mL of S-adenosyl-L-homocysteine hydrolase, 1.5 U/mL of uricase, 4.3 U/mL of xanthine oxidase, 6.4 U/mL of peroxidase, 2.9 mM of 4-aminoantipyrine, 2.3 mM of dithiothreitol and 0.2% Triton X-100 were added to 20 µL of 100 mM of phosphate buffer (pH7.4) and allowed to react for about 5 minutes. Then, 180 µL of a reagent 2 containing 100 mM of phosphate buffer (pH7.4), 0.3 U/mL of adenosine deaminase, 1.3 U/mL of purine nucleoside phosphorylase, 1.8 mM of TOOS, 17 mM of N-ethylmaleimide and 0.1% Triton X-100 were added thereto and allowed to react further for about 5 minutes. In parallel to this, the same operation was performed except that N-ethylmaleimide was not contained in the reagent 2, and the two reaction processes were compared. The results are shown in FIG. 3.

Figure 3:
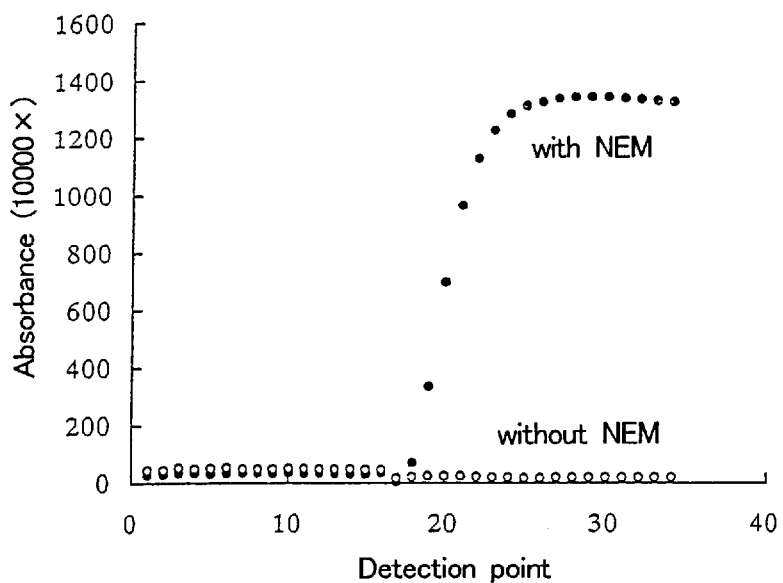
FIG. 3 is a graph showing the effects of adding an SH reagent on the color development in a homocysteine determination system by the use of an oxidative color-developing agent.

As seen from FIG. 3, in the absence of N-ethylmaleimide (NEM), the color development was significantly interfered, and determination was not possible at all (○). On the other hand, in the presence of N-ethylmaleimide (NEM), which is an SH reagent, a color was developed without being affected by the reducing reagent (●).

Example 4

Dose Dependence in the Case of Using a Homocystine Specimen as a Sample

Figure 4:
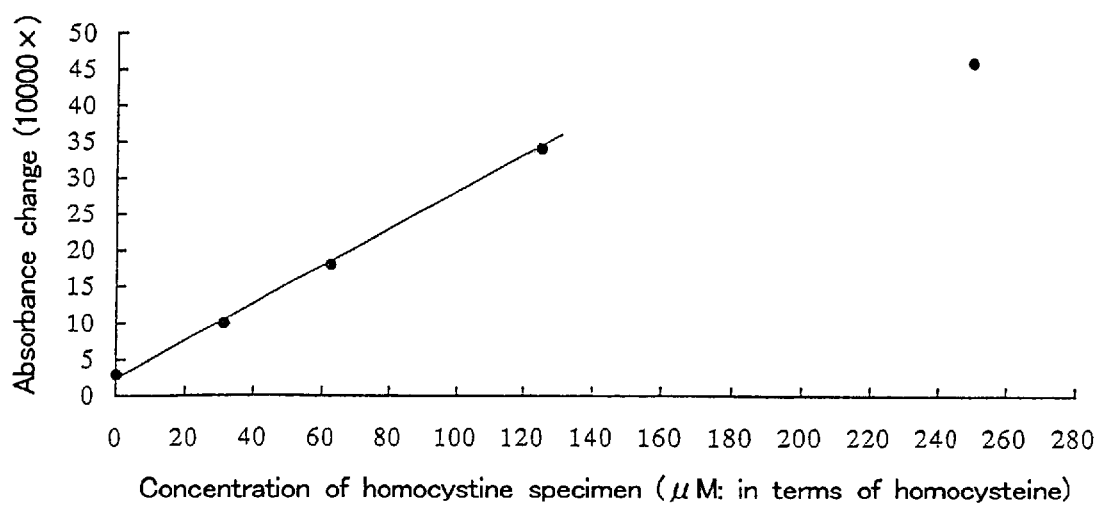
FIG. 4 is a graph showing the dose dependence when a homocystine specimen is used as a sample.

Determination was performed by using the Hitachi 7170 automatic analysis apparatus at a reaction temperature of 37° C., a dominant wavelength of 546 nm, and a secondary wavelength of 700 nm. First, 180 µL of a reagent 1 containing 100 mM of phosphate buffer (pH7.4), 0.7 U/mL of purine nucleoside phosphorylase, 2.7 U/mL of xanthine oxidase, 10 U/mL of peroxidase, 0.009 mM of adenosine, 1.8 mM of 4-aminoantipyrine, 1.8 mM of dithiothreitol, 0.4 U/mL of S-adenosyl-L-homocysteine hydrolase, and 0.5% Triton X-100 were added to 20 µL of a sample containing 100 mM of phosphate buffer (pH7.4) and 0, 15.625, 31.25, 62.5 or 125 µM of homocystine (0 to 250 µM in terms of homocysteine) and allowed to react for about 5 minutes. Then, 180 µL of a reagent 2 containing 100 mM of phosphate buffer (pH7.4), 2 mM of TOOS, 6 mM of N-ethylmaleimide, and 0.2 U/mL of adenosine deaminase were added thereto and allowed to react further for about 5 minutes. The absorbance change was obtained from the detection point 16 to 34 of the Hitachi 7170. The results are shown in FIG. 4. As seen from FIG. 4, there is a linear relationship between the absorbance change and the homocysteine concentration up to 125 µM, and it is found that the determination of homocysteine is possible.

Example 5

Homocysteine Determination in a Serum Sample (SAHase Method)

Determination was performed by using the Hitachi 7170 automatic analysis apparatus with a three reagent system at a reaction temperature of 37° C., a dominant wavelength of 546 nm, and a secondary wavelength of 700 nm. First, 50 μL of a reagent 1 containing 100 mM of phosphate buffer (pH7.4), 7 mM of dithiothreitol, 0.028 mM of adenosine and 0.3% Triton X-100 were added to 20 μL of a sample containing normal control serum SERACLEAR HE added with 0, 2.5, 5, 10, 20, 30, 40 or 50 μM of homocystine (0 to 100 μM in terms of homocysteine). Then, about 80 seconds later, 130 μL of a reagent 2 containing 100 mM of phosphate buffer (pH7.4), 2 U/mL of uricase, 1.6 U/mL of purine nucleoside phosphorylase, 5.9 U/mL of xanthine oxidase, 22 U/mL of peroxidase, 4 mM of 4-aminoantipyrine, 0.5 mM of dithiothreitol, 1.1 U/mL of S-adenosyl-L-homocysteine hydrolase, and 0.1% Triton X-100 were added thereto and allowed to react for about 8 minutes, so that adenosyl homocysteine was produced. At the same time, the effect of reaction intermediates derived from inosine contained in the sample on the determined value was avoided. Furthermore, 180 μL of a reagent 3 containing 100 mM of phosphate buffer (pH7.4), 1.8 mM of TOOS, 17 mM of N-ethylmaleimide, 0.23 U/mL of adenosine deaminase, and 0.1% Triton X-100 were added thereto and allowed to react further for about 5 minutes. The absorbance was detected immediately before the addition of the reagent 3 (at detection point 33 of Hitachi 7170) and 5 minutes after the addition (at detection point 50 of Hitachi 7170) and the change amount was obtained.

At the same time, a sample blank was determined. The same operation was performed, except that the reagent 2 (hereinafter, referred to as an "SAHase-added reagent") containing S-adenosyl-L-homocysteine hydrolase (which may be referred to as "SAHase" in the following) was replaced by a reagent having the same components as those of reagent 2 except SAHase (hereinafter, referred to as a "reagent without SAHase"). As described above, since a slight amount of adenosine deaminase is contaminated in the SAHase specimen, it is necessary to eliminate the effect. Therefore, at the same time, using 100 mM phosphate buffer (pH7.4) as a sample, a blank of the SAHase-added reagent and a blank of the reagent without SAHase were detected and the ratio thereof was used as a correction coefficient with respect to the effect of the contaminated adenosine deaminase.

Figure 5:
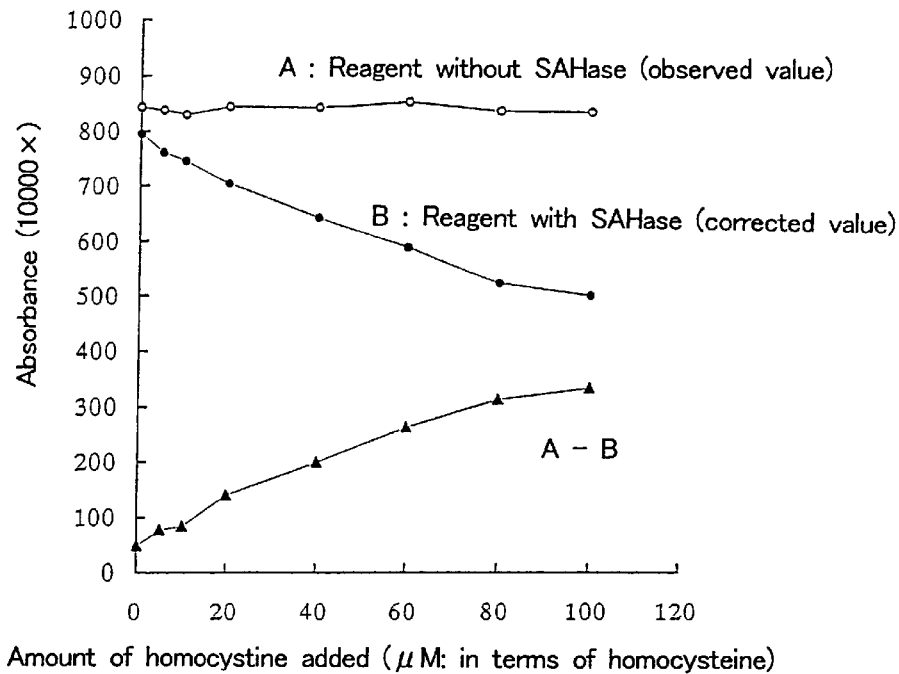
FIG. 5 is a graph showing the absorbance in each case where a reagent with S-adenosyl-L-homocysteine hydrolase added is used and where a reagent without it is used when determining homocysteine in a serum sample.
Figure 6:
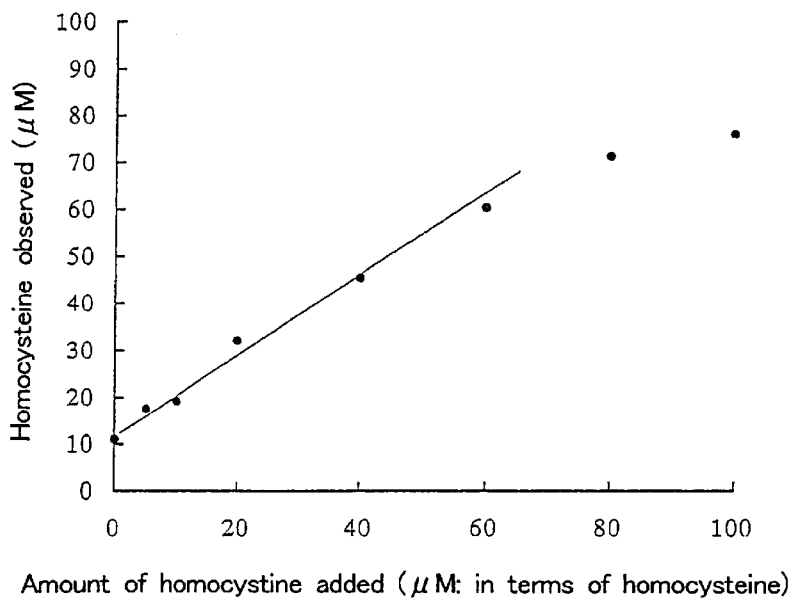
FIG. 6 is a graph showing the results of determining homocysteine in a serum sample.

FIG. 5 shows the result of plotting (A) the observed value using the reagent without SAHase, (B) the value corrected by multiplying the observed value using the SAHase-added reagent by the correction coefficient (hereinafter, the corrected value of the SAHase-added reagent), and (A–B) the value obtained by subtracting the corrected value of the SAHase-added reagent from the observed value of the reagent without SAHase, against the amount of the homocysteine added. The observed value of the reagent without SAHase is constant, regardless of the amount of the homocysteine added (A:○), whereas the corrected value of the SAHase-added reagent decreases depending on the amount of homocysteine added (B:●). Therefore, the value obtained by subtracting the corrected value of the SAHase-added reagent from the observed value of the reagent without SAHase depends on the amount of the homocysteine added (A–B:▲). On the other hand, a phosphate buffer containing 31.25 μM homocystine (62.5 μM in terms of homocysteine) was used as a sample, and each of the SAHase-added reagent and the reagent without SAHase is used as the reagent 2 for determination in the same manner and the values were corrected, so that the value (the difference in the absorbance) obtained by subtracting the corrected value of the SAHase-added reagent from the observed value of the reagent without SAHase was obtained, and a factor indicating the amount of the homocysteine per the absorbance difference was calculated. The amount of the homocysteine in each sample was calculated by multiplying the value (A–B in FIG. 5:▲) obtained by subtracting the corrected value of the SAHase-added reagent from the observed value of the reagent without SAHase in the serum-based sample by the factor. FIG. 6 shows the results of plotting the amount of the homocysteine against the amount of the homocysteine added (●).

As seen from FIG. 6, it is possible to determine the total homocysteine in serum until about 80 μM in the serum-based sample while avoiding the influence of the reaction intermediates derived from inosine contained in the sample and the endogenous adenosine or the like on the observed value.

Example 6
Effect of Cysteine and Methionine on the Homocysteine Determination System (SAHase Method)

Figure 7:
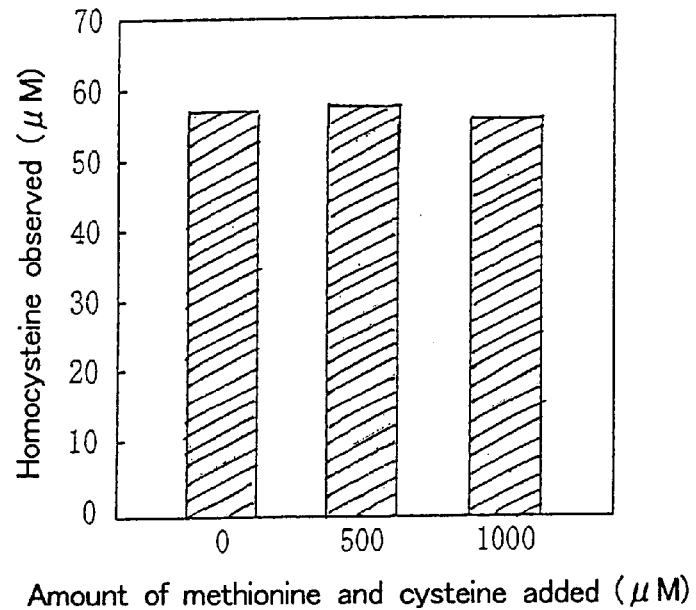
FIG. 7 is a graph showing the effect of cysteine and methionine on the homocysteine determination system.

Determination was performed in the same manner as in Example 5 except that a sample containing normal control serum SERACLEAR HE and 27 μM of homocystine (54 μM in terms of homocysteine), and samples in which 500 μM of methionine or 1000 μM of cysteine was added to this sample were used. As shown in FIG. 7, homocysteine can be determined accurately up to 1000 μM without any interference by cysteine and methionine.

Example 7
Correlation Between the the Present Invention (SAHase Method) and the Conventional HPLC Method For 53 serum samples, homocysteine was determined by the SAHase method. The determination was performed in the same manner as in Example 5, except that the followings were used: a control serum SERACLEAR HE containing 52.3 μM homocysteine as the standard; DA-67 as the color-developing reagent; and a dominant wavelength of 660 nm and a secondary wavelength of 750 nm. In other words, first, 50 μL of the reagent 1 containing 100 mM of phosphate buffer (pH 7.4), 7 mM of DTT, 0.015 mM of adenosine and 0.05% Triton X-100 were added to 10 μL of a serum sample. Then, about 80 seconds later, 130 μL of a reagent 2 containing 100 mM of phosphate buffer (pH7.4), 2 U/mL of uricase, 1.6 U/mL of purine nucleoside phosphorylase, 6 U/mL of xanthine oxidase, 150 U/mL of catalase, 0.84 mM of DA-67, 0.5 mM of DTT, 1.1 U/mL of SAHase, and 0.05% Triton X-100 were added thereto and allowed to react for about 8 minutes. Furthermore, 180 μL of a reagent 3 containing 100 mM of phosphate buffer (pH7.4), 11 U/mL of peroxidase, 17 mM of N-ethylmaleimide, 0.23 U/mL of adenosine deaminase, and 0.05% Triton X-100 were added thereto and allowed to react further for about 5 minutes. The detection point and the calibration were the same as in Example 5.

On the other hand, the homocysteine in the same samples was determined by the HPLC method (consigned to SRL Inc.).

Figure 8:
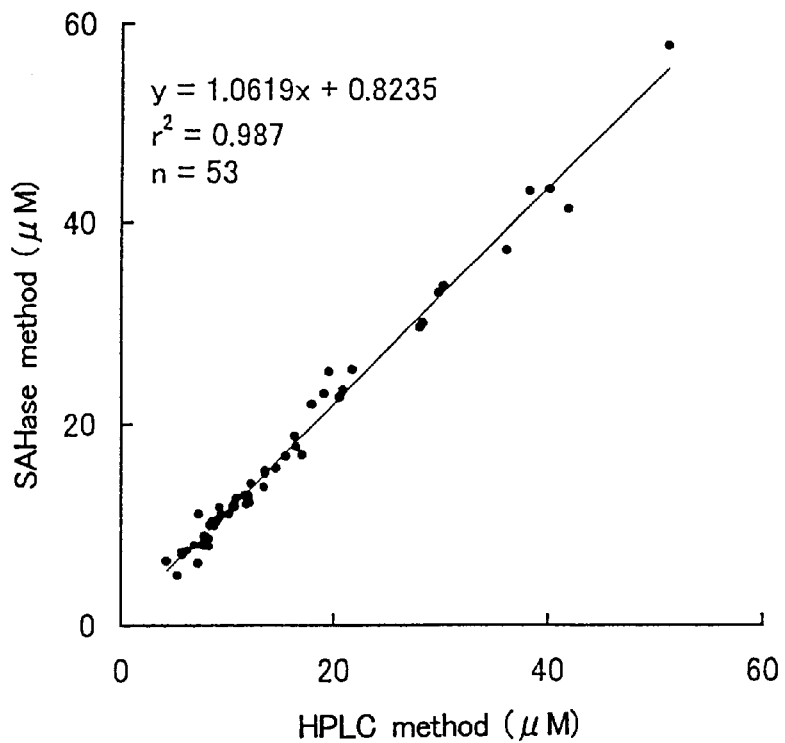
FIG. 8 is a graph showing the correlation of the values obtained by determining homocysteine in a serum sample by the method of the present invention (SAHase method) and the conventional HPLC method.

FIG. 8 shows the results of plotting the value obtained by the HPLC method on the horizontal axis and the value obtained by the method of the present invention (SAHase method) on the vertical axis. As seen from FIG. 8, a very good correlation is obtained, and the homocysteine in the sample can be determined accurately by the method of the present invention.

Example 8
Preparation of Homocysteine Methyltransferase

The method of S. K. Shapiro (Methods Enzymol., 17 Pt.B, 400–405, 1971) was partially modified to prepare a homocysteine methyltransferase enzyme solution in the following manner.

First, 250 g of baker's yeast (manufactured by Oriental Yeast Co., Ltd.) was suspended in 125 ml of distilled water, and heated to 37° C., and then 16.3 g of sodium hydrogencarbonate and 44 ml of toluene were added thereto with stirring. The mixture was incubated for 90 minutes with stirring at 37° C., and then an equal volume of ice-cooled distilled water was added thereto, and the mixture was cooled rapidly. This solution was centrifuged at 7000 rpm for 30 minutes. The supernatant was filtered through a paper towel and the filtrate was further centrifuged at 9000 rpm for 90 minutes, and the supernatant was collected.

Then, L-methionine was added with stirring under ice cooling such that the final concentration was 0.5%, and was dissolved over about 60 minutes. The temperature of the solution was kept at 3° C. or less, and ethanol cooled to about −20° C. was added at a rate of 20 mL/min with stirring. At the point when the concentration of ethanol reached about 25%, cooling was started by lowering the temperature of the cooling bath to −10° C. or less by using salt-ice. Then, ethanol was added in the same manner until the final concentration reached 53%, and then the solution was allowed to stand at −20° C. for 16 hours. Then, the solution was centrifuged at 9000 rpm and −10° C. for 60 minutes. The supernatant was collected, and ethanol was added under the same conditions until the final concentration reached 70% while cooling to −10° C. or less by using salt-ice. After the addition, the solution was allowed to stand for one hour, and centrifuged at 9000 rpm and −10° C. for 90 minutes.

The resultant precipitate was dissolved in about 7 mL of 10 mM of potassium phosphate buffer (pH 6.8). The dissolved solution was dialyzed twice against the same buffer, and then concentrated to about 1.5 mL with a centrifugal concentrator (Centriprep-10 manufactured by Amicon). Thus, an enzyme solution was obtained.

Then, the homocysteine methyltransferase activity of the obtained enzyme solution was determined in the following manner. First, 60 mM of phosphate buffer (pH 7.4), 10% of the enzyme solution, 1 mM of dithiothreitol, 0.2 mM of homocystine (H-6010 manufactured by Sigma-Aldrich Corp.), and 0.4 mM of iodinated L-methionine methyl sulfonium (27794-0250 manufactured by Across) or brominated D-methionine methyl sulfonium (29939-0010 manufactured by Across) were mixed and allowed to react at 37° C. for 2 hours. The mixture was spotted on a thin layer plate (plate for thin layer chromatography) in an amount of about 8 μL for each spot, and was developed with 95% ethanol-28% aqueous ammonia (77:23, v/v), and then color development was performed by ninhydrin. As a result, it was confirmed that in either case where L-methionine methyl sulfonium or D-methionine methyl sulfonium was used as the substrate, methionine was contained in the reaction product. On the other hand, it was confirmed that when homocysteine, which is a methyl acceptor, was removed from the reaction system, methionine was not produced.

From the above, it was confirmed that the obtained enzyme solution has homocysteine methyltransferase activity, and that this enzyme solution can utilize not only L-methionine methyl sulfonium, but also D-methionine methyl sulfonium as the methyl donor.

Figure 9:
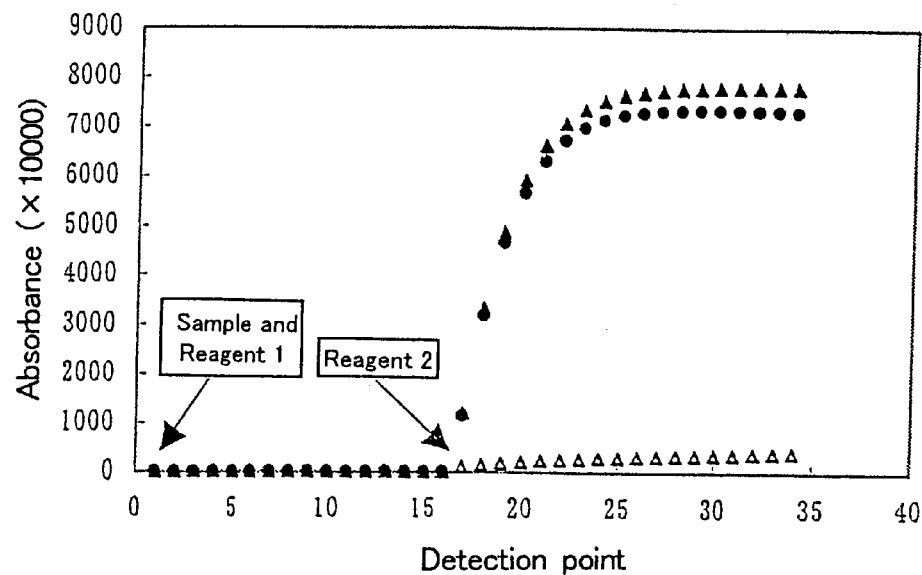
FIG. 9 is a graph showing the reaction time course of D-amino acid oxidase derived from porcine kidney with respect to D-methionine and D-methionine methyl sulfonium.

Example 9
Reactivity of D-amino Acid Oxidase Derived from Porcine Kidney with Respect to D-methionine and D-methionine Methyl Sulfonium The reactivity of D-amino acid oxidase derived from porcine kidney with respect to D-methionine and D-methionine methyl sulfonium was determined by using a Hitachi 7170 automatic analysis apparatus in the following manner. First, 200 μL of a reagent 1 containing 92 mM of phosphate buffer (pH7.4), 1.3 mM of 4-aminoantipyrine, and 3.3 U/mL of peroxidase were added to 10 μL of a sample containing 1.3 mM of D-methionine and allowed to react at 37° C. for about 5 minutes. Then, 50 μL of a reagent 2 containing 69 mM of phosphate buffer (pH7.4), 5.2 mM of TOOS, 2.6 U/mL of D-amino acid oxidase derived from porcine kidney (manufactured by Sigma-Aldrich Corp.), and 2.6 mM of flavin adenine dinucleotide (FAD) were added thereto and allowed to react further for about 5 minutes at 37° C. The absorbance change was detected at a dominant wavelength of 546 nm and a secondary wavelength of 700 nm. Furthermore, a sample containing 1.3 mM of brominated D-methionine methyl sulfonium and a sample containing 1.3 mM of D-methionine and 1.3 mM of brominated D-methionine methyl sulfonium were determined exactly in the same manner. FIG. 9 shows the time course of the reaction. The D-amino acid oxidase derived from porcine kidney was hardly reacted with D-methionine methyl sulfonium (Δ), compared with D-methionine (●). It was also found that the reactivity with D-methionine was not changed even in the presence of D-methionine methyl sulfonium (▲).

Figure 10:
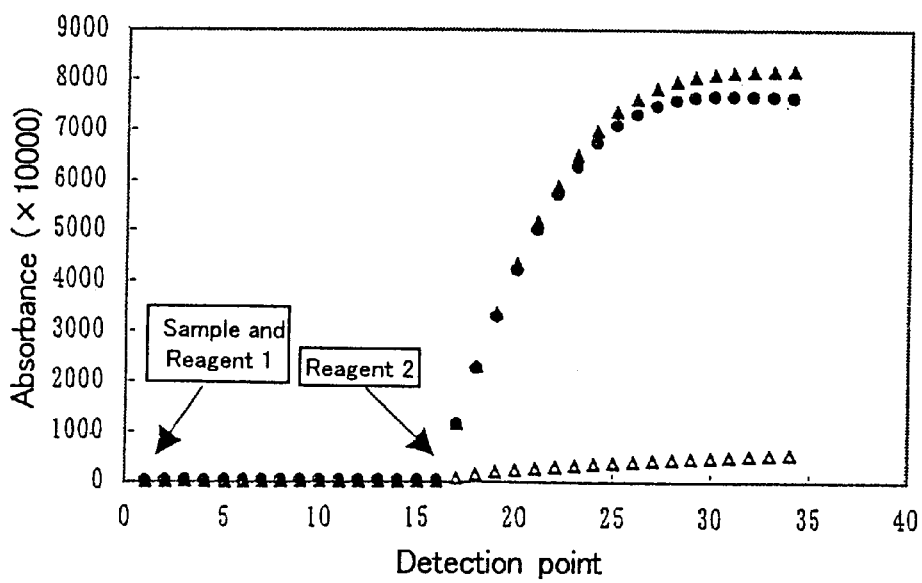
FIG. 10 is a graph showing the reaction time course of D-amino acid oxidase derived from fungi with respect to D-methionine and D-methionine methyl sulfonium.

Example 10
Reactivity of D-amino Acid Oxidase Derived from Fungi with Respect to D-methionine and D-methionine Methyl Sulfonium The reactivity was determined in the same manner as in Example 9, except that D-amino acid oxidase derived from porcine kidney was replaced by D-amino acid oxidase derived from fungi (Fusarium, manufactured by Ikedatohka Kogyo). FIG. 10 shows the time course of the reaction. It was evident that the D-amino acid oxidase derived from fungi also was hardly reacted with D-methionine methyl sulfonium (Δ), compared with D-methionine (●). Moreover, it was also found that the reactivity with D-methionine was not changed even in the presence of D-methionine methyl sulfonium (▲).

Example 11
Effect of N-ethylmaleimide on a D-methionine Determination System Employing an Oxidative Color-Developing Agent in the Presence of a Reducing Agent Next, D-methionine was determined by using a Hitachi 7170 automatic analysis apparatus in the following manner. First, 200 μL of a reagent 1 containing 100 mM of phosphate buffer (pH7.4), 1 mM of TOOS, and 0.05% Triton X-100 were added to 20 μL of 0, 0.0625, 0.125, 0.25, 0.5 or 1 mM of D-methionine containing 5 mM of dithiothreitol (DTT) and allowed to react at 37° C. for about 5 minutes. Then, 50 μL of a reagent 2 containing 100 mM of phosphate buffer (pH7.4), 4 mM of 4-aminoantipyrine, 1 U/mL of D-amino acid oxidase, 17.6 U/mL of peroxidase, 1 mM of FAD and 0.05% Triton X-100 were added thereto and allowed to react further for about 5 minutes at 37° C. The absorbance change (at a dominant wavelength of 546 nm and a secondary wavelength of 700 nm) from the detection point 16 to 34 was measured. Then, a reagent was prepared in the same manner except that 2.8 mM of N-ethylmaleimide (NEM) was added to the reagent 1, and the determination was performed for the case of the NEM addition in the same manner.

Figure 11:
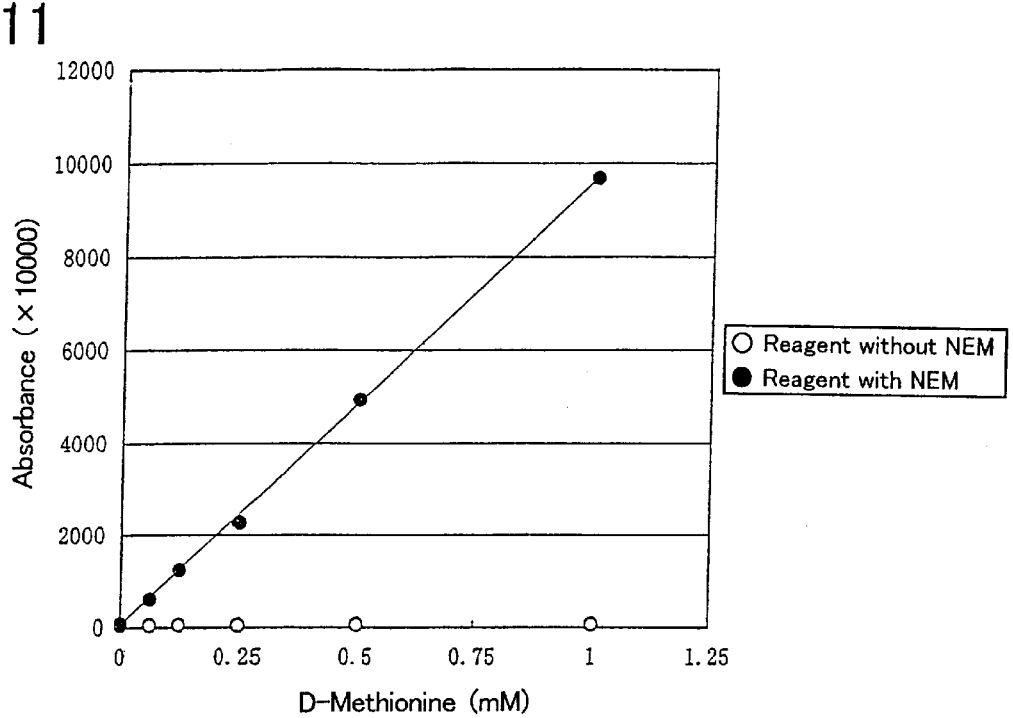
FIG. 11 is a graph showing the effects of an SH reagent on a D-methionine determination system by the use of an oxidative color-developing agent in the presence of a reducing agent.

As shown in FIG. 11, when the determination was performed by the use of the reagent without NEM (○), D-methionine was not detected at all because of the dithiothreitol contained in the sample. On the other hand, when the determination was performed by the use of the reagent with NEM (●), a linear dose dependence was recognized and it was found that the D-methionine can be determined.

Example 12
Examination of the Dose Dependence by the Use of a Homocysteine Specimen in the Method of the Present Invention (MTase Method I)

First, 0, 100, or 200 µM of homocystine (0, 200 or 400 µM in terms of homocysteine, respectively), 86 mM of phosphate buffer (pH 7.4), 10% of the enzyme solution, 4 mM of dithiothreitol and 1.5 mM of brominated D-methionine methyl sulfonium were reacted at 37° C. for 90 minutes.

The amount of the D-methionine in the reaction mixture was determined by using a Hitachi 7170 automatic analysis apparatus in the following manner. First, 200 µL of a reagent 1 containing 100 mM of phosphate buffer (pH7.4), 1 mM of TOOS, and 1.7 mM of N-ethylmaleimide (NEM) were added to 30 µL of the sample (reaction mixture) and allowed to react at 37° C. for about 5 minutes. Then, 50 µL of a reagent 2 containing 100 mM of phosphate buffer (pH7.4), 4 mM of 4-aminoantipyrine, 1 U/mL of D-amino acid oxidase, 17.6 U/mL of peroxidase, and 0.2 mM of FAD were added thereto and allowed to react further for about 5 minutes at 37° C. The absorbance change (at a dominant wavelength of 546 nm and a secondary wavelength of 700 nm) from the detection point 16 to 34 was measured. The results are shown in FIG. 12 with the homocystine concentration on the horizontal axis and the absorbance change (×10000) on the vertical axis.

Figure 12:
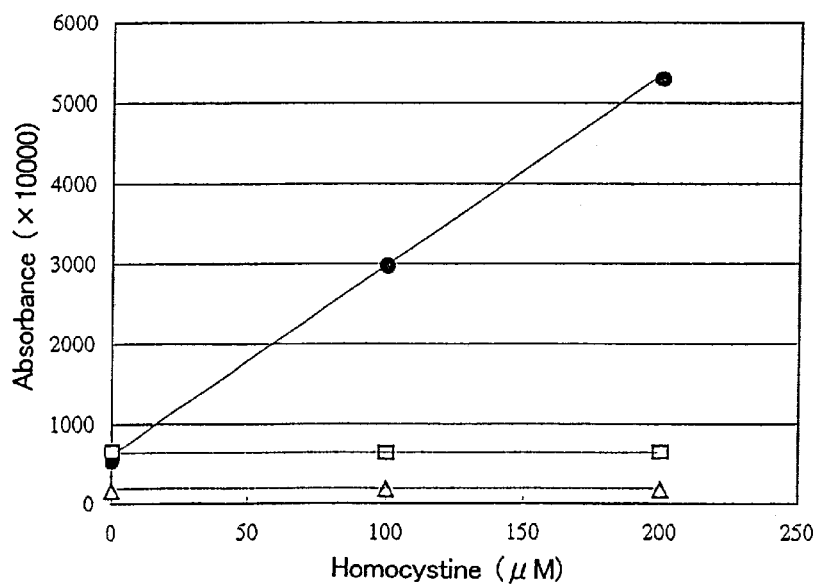
FIG. 12 is a graph showing the dose dependence when a homocystine specimen is used as a sample.

As seen from FIG. 12, the absorbance change increases depending on the homocystine dose (●). On the other hand, when D-methionine methyl sulfonium was not added (△), and when the enzyme was not added (□), the dose dependence was not seen.

Example 13
Examination of the Dose Dependence of Serum Homocysteine in the Method of the Present Invention (MTase Method I)

First, 50 µL of a treatment solution containing 50 mM of phosphate buffer (pH 7.4), 30% of the enzyme solution, 15 mM of dithiothreitol and 3 mM of brominated D-methionine methyl sulfonium were added to 100 µL of a sample in which 0, 10, 20, 30, 40 or 50 µM of homocystine (0 to 100 µM in terms of homocysteine) was added to normal control serum SERACLEAR HE (AZWELL Inc.), mixed therewith, and allowed to react at 37° C. for 90 minutes.

The amount of the D-methionine in the reaction mixture was determined by using a Hitachi 7170 automatic analysis apparatus in the following manner. First, 200 µL of a reagent 1 containing 100 mM of phosphate buffer (pH7.4), 1 mM of TOOS, 2.8 mM of NEM and 0.05% Triton X-100 were added to 20 µL of the sample (reaction mixture) and allowed to react at 37° C. for about 5 minutes. Then, 50 µL of a reagent 2 containing 100 mM of phosphate buffer (pH7.4), 4 mM of 4-aminoantipyrine, 1 U/mL of D-amino acid oxidase, 17.6 U/mL of peroxidase, 1 mM of FAD and 0.05% Triton X-100 were added thereto and allowed to react further for about 5 minutes at 37° C. The absorbance change (at a dominant wavelength of 546 nm and a secondary wavelength of 700 nm) from the detection point 16 to 34 was measured. The results are shown in FIG. 13 with the added homocystine concentration on the horizontal axis and differences in absorbance on the vertical axis, in which the differences were obtained by subtracting the absorbance change (×10000) in the sample without homocystine from the absorbance change (×10000) in each sample.

Figure 13:
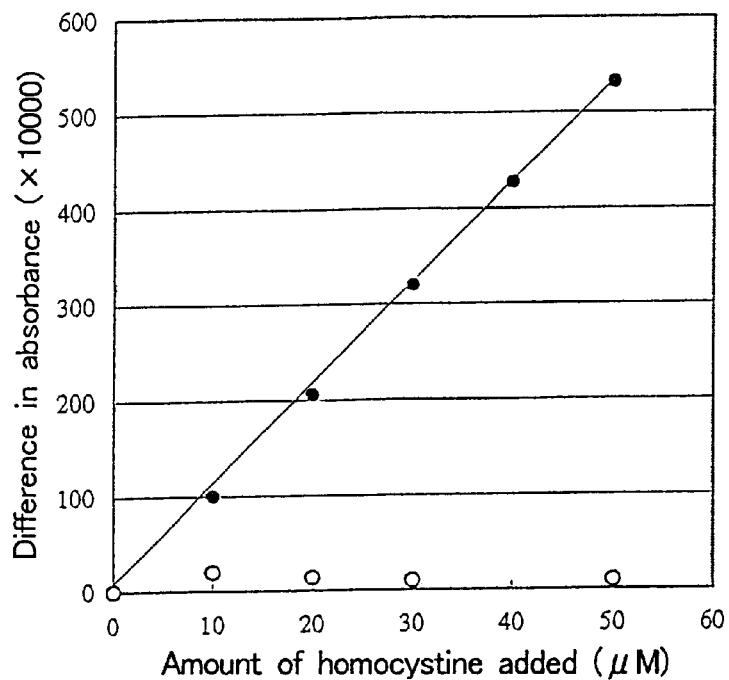
FIG. 13 is a graph showing the absorbance in each case where a reagent with D-methionine methyl sulfonium added is used and where a reagent without it is used when determining homocysteine in a serum sample.

As seen from FIG. 13, the dose dependence on the amount of the homocystine added was also found in the serum sample (●). On the other hand, when D-methionine methyl sulfonium was not added (○), such a dependence was not found. The above-described results make it evident that the amount of the homocysteine in the sample can be quantitatively determined.

Figure 14:
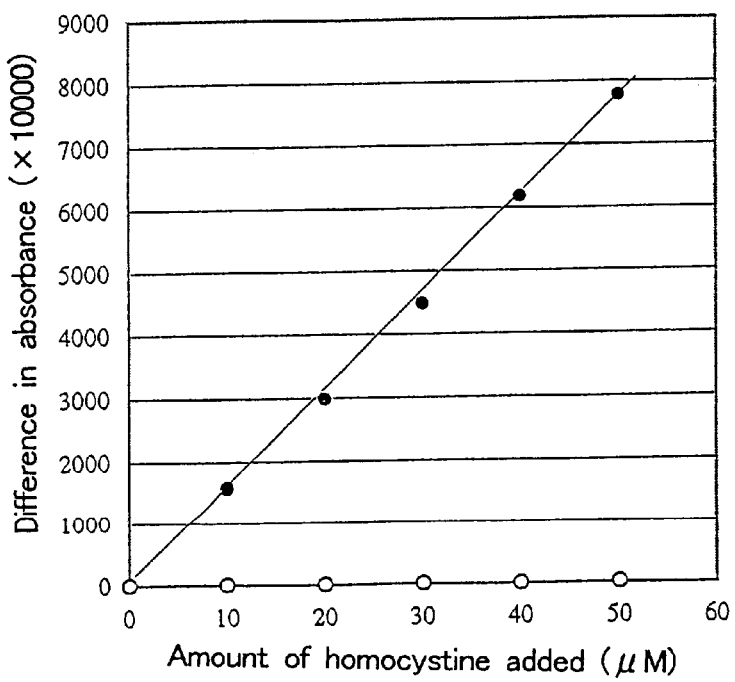
FIG. 14 is a graph showing the results of determining homocysteine in a serum sample using a highly sensitive color-developing agent.

Example 14
Determination by the Use of a Highly Sensitive Color-Developing Agent Determination was performed exactly in the same manner as in Example 13, except that a TOOS and 4-aminoantipyrine system as the color-developing agent for quantitative determination of D-methionine were replaced by TPM-PS, which is a highly sensitive color-developing agent. More specifically, a reagent obtained by removing TOOS from the reagent 1 for quantitative determination of D-methionine, and a reagent obtained by removing 4-animo antipyrine from the reagent 2 and adding 2 mM of TMP-PS instead were used for determination. As shown in FIG. 14, the determination by the use of TMP-PS can be performed with higher sensitivity than the determination by the use of the TOOS and 4-aminoantipyrine system.

Example 15
Correlation Between the Present Invention (MTase Method I) and the Conventional HPLC Method.

For 35 serum samples, homocysteine was determined by the MTase method I. A saline was used as a reagent blank, and a saline containing 50 µM homocysteine was used as a standard. First, 50 µL of 35 mM of phosphate buffer (pH 7.0) containing 9.6 U/L homocysteine methyltransferase, 15 mM DTT, 1.5 mM of brominated D-methionine methyl sulfonium and 0.5 mM of zinc bromide were added to 100 µL of a sample and allowed to react at 37° C. for 90 minutes. It should be noted that 1 U of homocysteine methyltransferase is the amount of enzyme that catalyzes D-methionine synthesis in an amount of 1 µmol per minute when D-methionine methyl sulfonium is used as the methyl donor and homocysteine is used as a methyl acceptor. The same sample was reacted with a reagent that does not contain homocysteine methyltransferase in the same manner. Then, 150 µL of a solution containing 18 mM of NEM was added thereto to stop the reaction. The amount of the D-methionine in the reaction mixture was determined by using a Hitachi 7170 automatic analysis apparatus in the following manner. First, 150 µL of 96 mM of phosphate buffer (pH7.0) containing 0.48 mM of TOOS were added to 30 µL of the reaction mixture and allowed to react at 37° C. for about 5 minutes. Then, 100 µL of 90 mM of phosphate buffer (pH7.0) containing 0.7 mM of 4-aminoantipyrine, 1.4 U/mL of D-amino acid oxidase, 4.4 U/mL of peroxidase, and 1 mM of FAD were added thereto and allowed to react further for about 5 minutes at 37° C. The absorbance change (at a dominant wavelength of 546 nm and a secondary wavelength of 700 nm) from the detection point 16 to 34 was measured. The amount of the homocysteine in the sample was calculated using a value obtained by subtracting the absorbance change in the reagent without homocysteine methyltransferase (sample blank) from the absorbance change in the reagent with this enzyme.

On the other hand, the homocysteine in the same sample was determined by the HPLC method (consigned to SRL Inc.).

Figure 15:
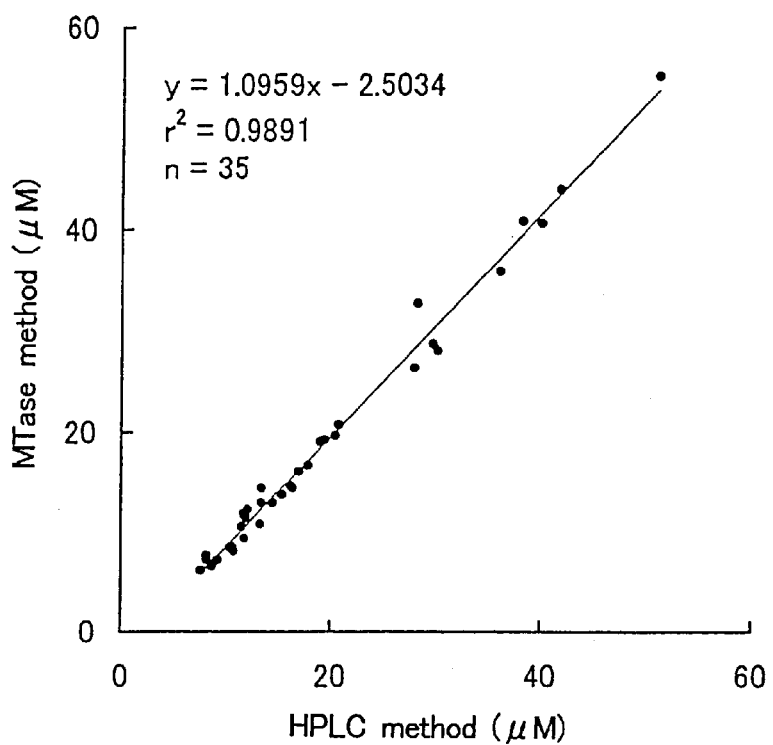
FIG. 15 is a graph showing the correlation of the values obtained by determining homocysteine in a serum sample by the method of the present invention (MTase method I) and the conventional HPLC method.

The results are shown in FIG. 15 with the value obtained by the HPLC method on the horizontal axis and the value obtained by the method of the present invention (MTase method I) on the vertical axis. As seen from FIG. 15, a very satisfactory correlation is obtained, and the homocystine in the samples can be determined accurately by the method of the present invention.

Example 16
Dose Dependency in the D-methionine Determination System using D-amino Acid Oxidase and Leucine Dehydrogenase and the Effect of a Reducing Agent, DTT The D-methionine was determined by the use of a Hitachi 7170 automatic analysis apparatus in the following manner. First, 180 µL of a reagent 1 containing 50 mM of TAPS (N-tris(hydroxymethyl)methyl-3-aminopropane sulfonic acid; manufactured by Dojin Kagaku Kenkyusho) (pH8.5), 990 mM of ammonium chloride (manufactured by Nakarai), 3.4 U/mL leucine dehydrogenase (manufactured by Wako Pure Chemical Industries, Ltd.), 32 U/ml of catalase (manufactured by Roche) and 0.16 mM of NADH (manufactured by Oriental Yeast Co., Ltd.) were added to 30 µL of a sample containing 0, 25, 50, 100, 200 or 400 µM of D-methionine in a saline (0.9% NaCl) and allowed to react at 37° C. for about 5 minutes. Then, 40 µL of a reagent 2 containing 50 mM of TAPS (pH8.5), 990 mM of ammonium chloride, 5 U/mL of D-amino acid oxidase (derived from porcine kidney, manufactured by Kikkoman) and 0.1 mg/mL of FAD were added thereto and allowed to react further for about 5 minutes at 37° C. The absorbance change (at a dominant wavelength of 340 nm and a secondary wavelength of 405 nm) of NADH from the detection point 16 to 34 was measured. Next, a reagent was prepared exactly in the same manner except that 10 mM of DTT was added to the reagent 1, and the determination by the use of DTT was performed in the same manner.

Figure 16:
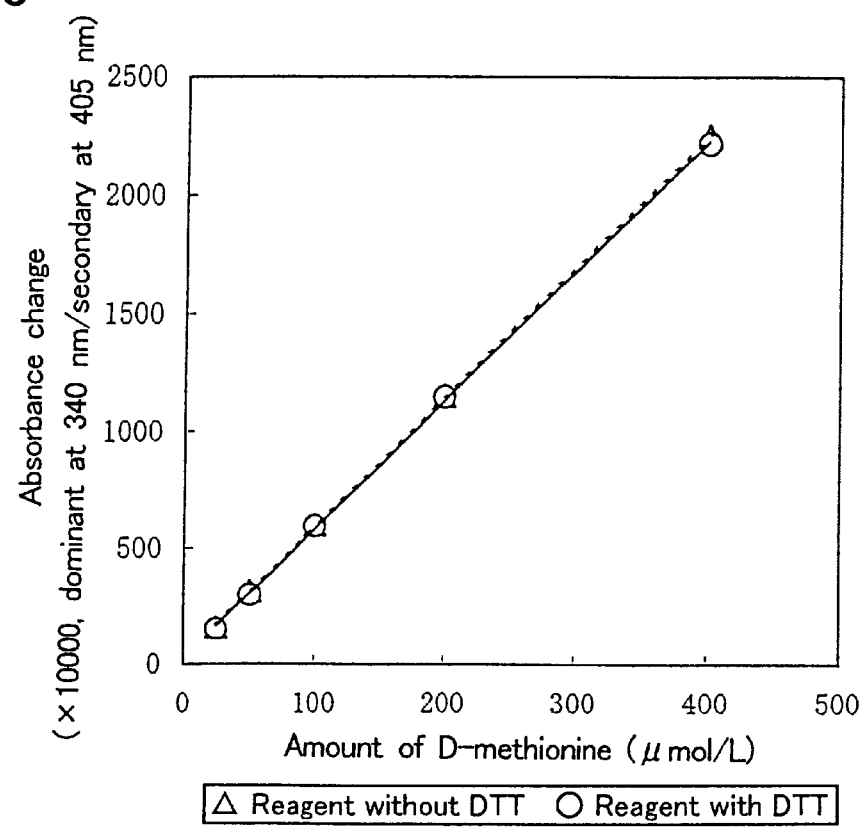
FIG. 16 is a graph showing the dose dependence in a D-methionine determination system by the use of D-amino acid oxidase and leucine dehydrogenase.

The results are shown in FIG. 16 with the D-methionine concentration on the horizontal axis and the absorbance change at 340 nm (secondary wavelength of 405 nm) on the vertical axis.

As seen from FIG. 16, when DTT was not added (Δ), the D-methionine dose-dependent linear absorbance change was observed in this determination system, so that D-methionine can be quantitatively determined. When DTT was added (○), the determination of D-methionine was not affected by DTT.

Example 17
Dose Dependency in the Homocysteine Determination System (MTase Method II) using Homocysteine Methyltransferase, D-amino Acid Oxidase and Leucine Dehydrogenase Homocysteine was determined by the use of a Hitachi 7170 automatic analysis apparatus in the following manner. First, 180 µL of a reagent 1 containing 50 mM of TAPS (pH8.5), 990 mM of ammonium chloride, 10 mM of DTT, 0.5 U/mL of homocysteine methyltransferase (derived from yeast, obtained from Ozeki), 0.6 mM of brominated D-methionine methyl sulfonium, 5 U/mL leucine dehydrogenase (manufactured by Wako Pure Chemical Industries, Ltd.), 32 U/ml of catalase and 0.16 mM of NADH were added to 30 µL of a sample containing 0, 12.5, 25, 50, or 100 µM of homocystine (0, 25, 50, 100 or 200 µM in terms of homocysteine) in a saline (0.9% NaCl) and allowed to react at 37° C. for about 5 minutes. Then, 40 µL of a reagent 2 containing 50 mM of TAPS (pH8.5), 990 mM of ammonium chloride, 7.5 U/mL of D-amino acid oxidase (manufactured by Kikkoman) and 0.1 mg/mL of FAD were added thereto and allowed to react further for about 5 minutes at 37° C. The absorbance change (at a dominant wavelength of 340 nm and a secondary wavelength of 405 nm) in NADH from the detection point 16 to 34 was measured. Next, determination was performed exactly in the same manner as above except that a sample in which 0, 12.5, 25, 50 or 100 µM of homocystine was added to a normal control serum SERACLEAR HE was used as the sample.

Figure 17:
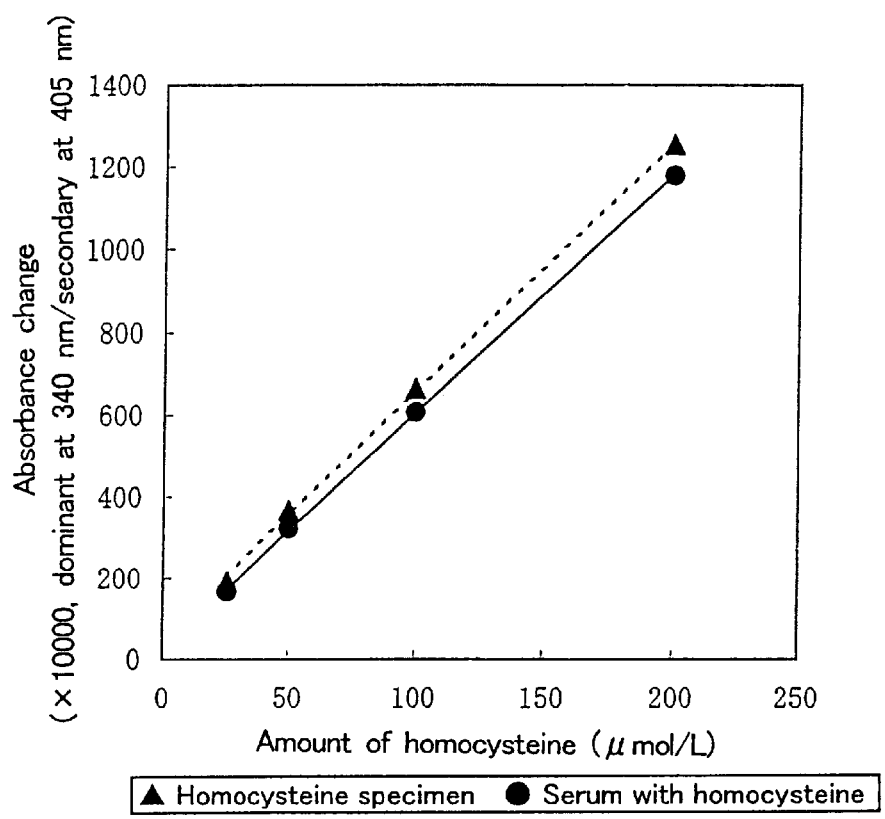
FIG. 17 is a graph showing the dose dependence in a homocysteine determination system (the method of the present invention: MTase method II) by the use of homocysteine methyltransferase, D-amino acid oxidase and leucine dehydrogenase.

The results are shown in FIG. 17 with the concentration of the added homocysteine on the horizontal axis and the absorbance change at 340 nm (secondary wavelength of 405 nm) on the vertical axis.

As seen from FIG. 17, in both the cases of the homocysteine specimen (●) and the serum sample (▲), it can be seen that the absorbance change depends on the dose of the homocysteine added, so that it is evident that also in this determination system, homocysteine can be quantitatively determined.

Example 18
Dose Dependency in the Homocysteine Determination System (MTase Method II) Using Homocysteine Methyltransferase, D-amino Acid Oxidase and Glutamate Dehydrogenase Homocysteine was determined by using a Hitachi 7170 automatic analysis apparatus in the following manner. First, 180 µL of a reagent 1 containing 100 mM of Tris buffer (pH8.0), 10 mM of DTT, 0.6 mM of brominated D-methionine methyl sulfonium, 2 U/mL D-amino acid oxidase (manufactured by Kikkoman), 0.03 mg/mL of FAD, 32 U/ml of catalase, 8 U/mL of glutamate dehydrogenase (manufactured by Toyobo Co., Ltd.), 8 mM of 2-oxoglutaric acid (manufactured by Nakarai), and 0.16 mM of NADH were added to 30 µL of a sample containing 0, 12.5, 25, 50, or 100 µM of homocystine (0, 25, 50, 100 or 200 µM in terms of homocysteine) in a saline (0.9% NaCl) and allowed to react at 37° C. for about 5 minutes. Then, 40 µL of a reagent 2 containing 100 mM of Tris buffer (pH8.0) and 2.1 U/mL of homocysteine methyltransferase (derived from yeast, obtained from Ozeki) were added thereto and allowed to react further for about 5 minutes at 37° C. The absorbance change (at a dominant wavelength of 340 nm and a secondary wavelength of 405 nm) in NADH from the detection point 16 to 34 was measured. Next, determination was performed in the same manner as above except that a sample in which 0, 12.5, 25, 50 or 100 µM of homocystine was added to a normal control serum SERACLEAR HE was used.

Figure 18:
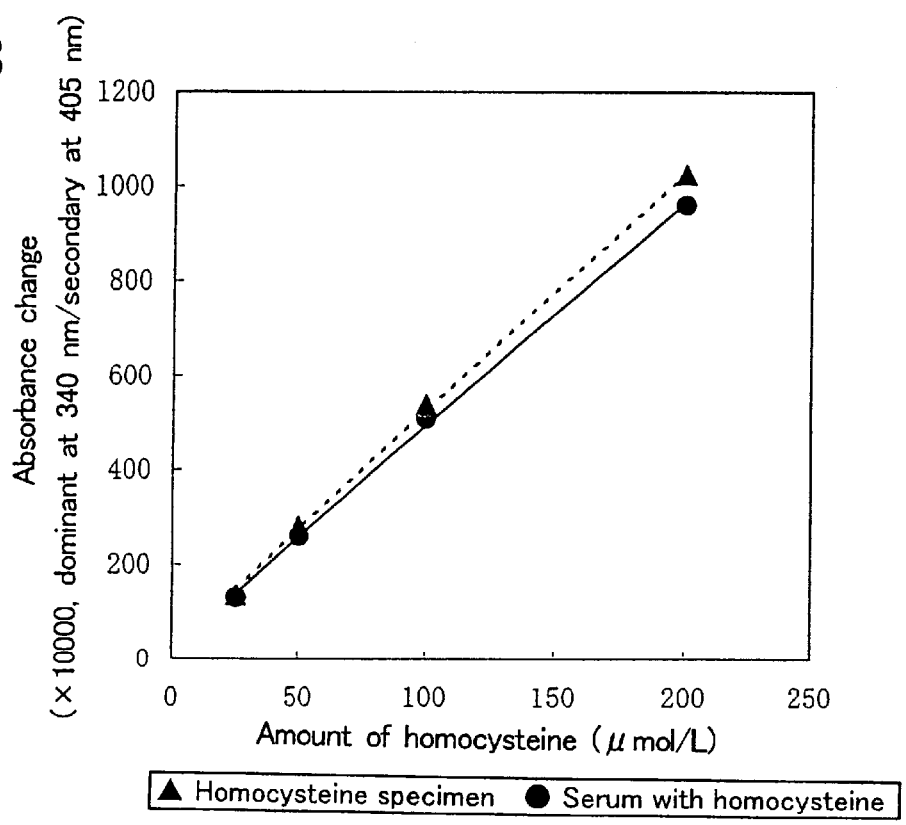
FIG. 18 is a graph showing the dose dependence in a homocysteine determination system (the method of the present invention: MTase method II) by the use of homocysteine methyltransferase, D-amino acid oxidase and glutamate dehydrogenase.

The results are shown in FIG. 18 with the concentration of the added homocysteine on the horizontal axis and the absorbance change at 340 nm (secondary wavelength of 405 nm) on the vertical axis.

As seen from FIG. 18, in both the cases of the homocysteine specimen (●) and the serum sample (▲), it can be seen that the absorbance change depends on the dose of the homocysteine added. It is evident that also in this determination system, homocysteine can be quantitatively determined.

Example 19
Quantitativity of 4-methylthio-2-oxobutyric Acid by Lactate Dehydrogenase 4-Methylthio-2-oxobutyric acid was determined by using a Hitachi 7170 automatic analysis apparatus in the following manner. First, 180 µL of a reagent 1 containing 200 mM of phosphate buffer (pH7.0) and 0.16 mM of NADH were added to 30 µL of a sample containing 0, 50, 100, 200 or 400 µM of 4-methylthio-2-oxobutyric acid in a saline (0.9% NaCl) and allowed to react at 37° C. for about 5 minutes. Then, 40 µL of a reagent 2 containing 200 mM of phosphate buffer (pH7.0) and 65 U/mL of lactate dehydrogenase (derived from porcine heart, manufactured by Oriental Yeast) were added thereto and allowed to react further for about 5 minutes at 37° C. The absorbance change (at a dominant wavelength of 340 nm and a secondary wavelength of 405 nm) in NADH from the detection point 16 to 34 was measured.

Figure 19:
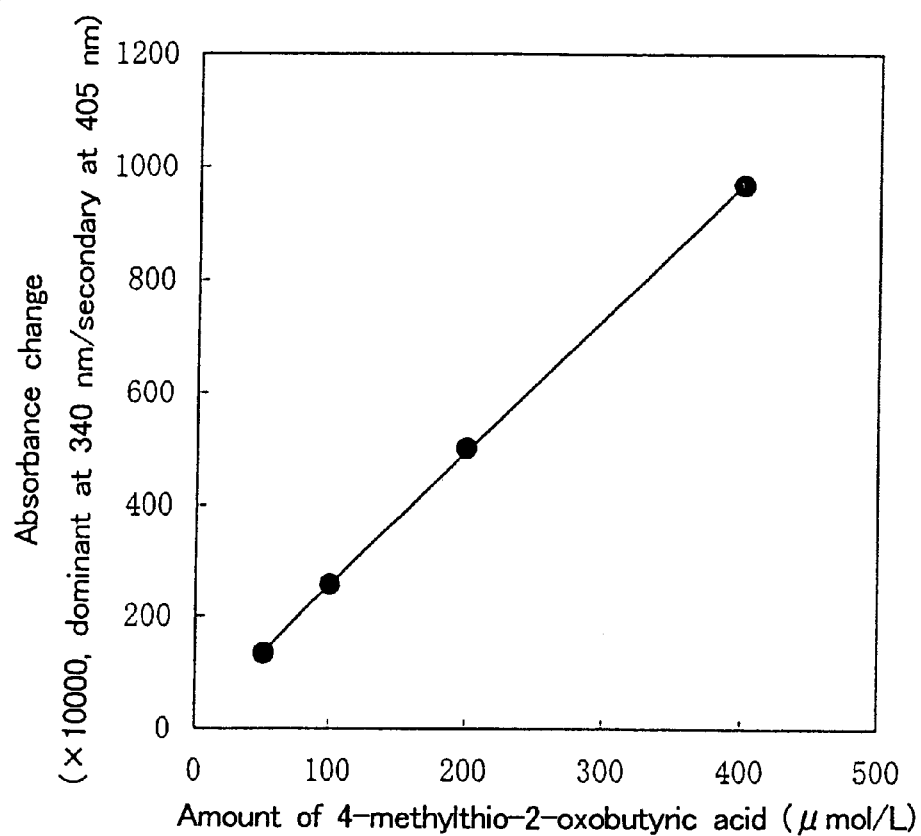
FIG. 19 is a graph showing the dose dependence in a 4-methylthio-2-oxobutyric acid determination system by the use of lactate dehydrogenase.

The results are shown in FIG. 19 with the 4-methylthio-2-oxobutyric acid concentration on the horizontal axis and the absorbance change at 340 nm (secondary wavelength of 405 nm) on the vertical axis.

As seen from FIG. 19, it can be seen that the absorbance change depends on the dose of the 4-methylthio-2-oxobutyric acid, so that it is evident that the lactate dehydrogenase uses 4-methylthio-2-oxobutyric acid as the substrate, and also in this determination system where the lactate dehydrogenase is used instead of the leucine dehydrogenase and the glutamate dehydrogenase in Examples 17 and 18, homocysteine can be quantitatively determined.

Based on the above description, it is readily appreciate that the present invention allows homocysteine in a biological sample, in particular, in body fluids such as blood and urine to be detected and quantitatively determined rapidly and simply and with high sensitivity.

What is claimed is:

1. A method for detecting or determining homocysteine in a sample, comprising:
   (a) reducing the homocysteine in the sample with a thiol compound,
   (b) reacting the reduced homocysteine with a homocysteine-converting enzyme and a homocysteine cosubstrate, thereby producing a homocysteine converting enzyme product, and
   (c) detecting or determining the residual homocysteine cosubstrate, the produced homocysteine-converting enzyme product or an enzyme reaction product thereof by (i) oxidizing the residual homocysteine cosubstrate, the produced homocysteine-converting enzyme product or an enzyme reaction product thereof in the presence of an SH reagent to produce hydrogen peroxide and detecting or determining the produced hydrogen peroxide by color development using an oxidative color-developing agent or (ii) reacting the residual homocysteine cosubstrate, the produced homocysteine-converting enzyme product or an enzyme reaction product thereof with a D-amino acid converting enzyme to produce an oxo acid and/or ammonia and detecting or determining the produced oxo acid and/or ammonia.

2. The method of claim 1, wherein the homocysteine-converting enzyme in the step (b) is S-adenosyl-L-homocysteine hydrolase, and the homocysteine cosubstrate in the steps (b) and (c) is adenosine.

3. The method of claim 2, wherein the step (c) of detecting or determining the adenosine is a step of detecting or determining the adenosine by reacting the adenosine with adenosine deaminase, phosphoric acid, purine nucleoside phosphorylase, and xanthine oxidase to produce hydrogen peroxide and detecting or determining the produced hydrogen peroxide by color development using peroxidase and an oxidative color-developing agent.

4. The method of claim 1, wherein the homocysteine-converting enzyme in the step (b) is a methyltransferase using homocysteine as a methyl acceptor, and the homocysteine cosubstrate in the steps (b) and (c) is a methyl donor.

5. The method of claim 4, wherein the methyltransferase is homocysteine methyltransferase, and the methyl donor is D-methionine methyl sulfonium.

6. The method of claim 4, wherein the D-amino acid converting enzyme is D-amino acid oxidase.

7. The method of claim 4, wherein in the step (c), the produced hydrogen peroxide is detected or determined by color development using peroxidase and an oxidative color-developing agent.

8. The method of claim 4, wherein in the step (c), a decrease in NAD(P)H or an increase in NAD(P) is detected or determined by reacting the produced oxo acid and/or ammonia with dehydrogenase using NAD(P)H as a coenzyme.

9. A reagent kit for homocysteine determination comprising a thiol compound, a homocysteine-converting enzyme, a homocysteine cosubstrate, an SH reagent, and an oxidative color-developing agent.

10. The kit of claim 9, wherein the homocysteine-converting enzyme is S-adenosyl-L-homocysteine hydrolase, and the homocysteine cosubstrate is adenosine.

11. The kit of claim 10, further comprising adenosine deaminase, phosphoric acid, purine nucleoside phosphorylase, xanthine oxidase, and peroxidase.

12. A reagent kit for homocysteine determination comprising a thiol compound, a homocysteine-converting enzyme, a homocysteine cosubstrate, and a D-amino acid converting enzyme.

13. The kit of claim 12, further comprising NAD(P)H, dehydrogenase using NAD(P)H as a coenzyme, and an ammonium salt or 2-oxo acid as its cosubstrate.

14. The kit of claim 9, wherein the homocysteine-converting enzyme is a methyltransferase using homocysteine as a methyl acceptor, and the homocysteine cosubstrate is a methyl donor.

15. The kit of claim 14, wherein the methyltransferase is homocysteine methyltransferase, and the methyl donor is D-methionine methyl sulfonium.

16. The kit of claim 12, wherein the D-amino acid converting enzyme is D-amino acid oxidase.

17. The method of claim 5, wherein the D-amino acid converting enzyme is D-amino acid oxidase.

18. The method of claim 5, wherein in the step (c), the produced hydrogen peroxide is detected or determined by color development using peroxidase and an oxidative color-developing agent.

19. The method of claim 6, wherein in the step (c), the produced hydrogen peroxide is detected or determined by color development using peroxidase and an oxidative color-developing agent.

20. The method of claim 5, wherein in the step (c), a decrease in NAD(P)H or an increase in NAD(P) is detected or determined by reacting the produced oxo acid and/or ammonia with dehydrogenase using NAD(P)H as a coenzyme.

21. The method of claim 6, wherein in the step (c), a decrease in NAD(P)H or an increase in NAD(P) is detected or determined by reacting the produced oxo acid and/or ammonia with dehydrogenase using NAD(P)H as a coenzyme.

22. The kit of claim 12, wherein the homocysteine-converting enzyme is a methyltransferase using homocysteine as a methyl acceptor, and the homocysteine cosubstrate is a methyl donor.

23. The kit of claim 13, wherein the homocysteine-converting enzyme is a methyltransferase using homocysteine as a methyl acceptor, and the homocysteine cosubstrate is a methyl donor.

24. The kit of claim 13, wherein the D-amino acid converting enzyme is D-amino acid oxidase.

25. The kit of claim 14, wherein the D-amino acid converting enzyme is D-amino acid oxidase.

26. The kit of claim 15, wherein the D-amino acid converting enzyme is D-amino acid oxidase.

* * * * *

UNITED STATES PATENT AND TRADEMARK OFFICE
CERTIFICATE OF CORRECTION

PATENT NO. : 6,686,172 B2  
DATED : February 3, 2004  
INVENTOR(S) : Naoto Matsuyama et al.

It is certified that error appears in the above-identified patent and that said Letters Patent is hereby corrected as shown below:

Title page,  
Item [57], ABSTRACT,  
Line 1, "The present invention provides a method" should read -- A method --.  
Line 3, "by oxidizing" should read -- comprising oxidizing --.

Column 1,  
Line 3, after the title, insert: -- This application is a 371 of PCT/JP01/05679, filed June 29, 2001, which claims priority to foreign application numbers JP 2000-198094, filed June 30, 2000, and JP 2000-280713, filed September 14, 2000. --

Column 23,  
Line 11, "appreciate" should read -- appreciated --.

Signed and Sealed this

Sixth Day of July, 2004

JON W. DUDAS  
*Acting Director of the United States Patent and Trademark Office*